United States Patent
Ishihara et al.

(10) Patent No.: US 8,546,079 B2
(45) Date of Patent: Oct. 1, 2013

(54) REPORTER GENE CONSTRUCT, ASSAY KIT AND DETECTION METHOD

(75) Inventors: Mitsuko Ishihara, Tokyo (JP); Hiroyuki Kayano, Fujisawa (JP); Eiichi Akahoshi, Tokyo (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 42 days.

(21) Appl. No.: 13/072,301

(22) Filed: Mar. 25, 2011

(65) Prior Publication Data

US 2012/0077203 A1 Mar. 29, 2012

(30) Foreign Application Priority Data

Sep. 24, 2010 (JP) ................................. 2010-214480

(51) Int. Cl.
*C12Q 1/68* (2006.01)
*G01N 33/53* (2006.01)

(52) U.S. Cl.
USPC ......... 435/6.1; 435/6.13; 435/6.16; 435/6.18; 435/7.72

(58) Field of Classification Search
None
See application file for complete search history.

(56) References Cited

U.S. PATENT DOCUMENTS

| 2002/0099026 A1* | 7/2002 | Goodman et al. | 514/44 |
| 2002/0197653 A1* | 12/2002 | Shair et al. | 435/7.21 |
| 2007/0032453 A1* | 2/2007 | Towner et al. | 514/62 |

FOREIGN PATENT DOCUMENTS

JP 2002-238599 8/2002

OTHER PUBLICATIONS

Srausberg et al., Generation and initial analysis of more than 15,000 full-length human and mouse cDNA sequences; PNAS, vol. 99, No. 26, 16899-16903, 2002.*
Genbank Accession No. BC062378.1 Mouse iNOS2 sequence, accessed Jan. 7, 2013.*
Linda J. Roman et al., "The C Terminus of Mouse Macrophage Inducible Nitric-oxide Synthase Attenuates Electron Flow through the Flavin Domain", The Journal of Biological Chemistry, vol. 275, No. 29, Issue of Jul. 21, 2000, pp. 21914-21919.
Giselle M. Knudsen et al., "Nitric-oxide Synthase (NOS) Reductase Domain Models Suggest a New Control Element in Endothelial NOS That Attenuates Calmodulin-dependent Activity", The Journal of Biological Chemistry, vol. 278, No. 34, Issue of Aug. 22, 2003, pp. 31814-31824.
U.S. Appl. No. 13/072,072, filed Mar. 25, 2011, Kayano.

* cited by examiner

*Primary Examiner* — Celine Qian
*Assistant Examiner* — Addison D Ault
(74) *Attorney, Agent, or Firm* — Oblon, Spivak, McClelland, Maier & Neustadt, L.L.P.

(57) ABSTRACT

According to one embodiment, there is provided a reporter gene construct. The reporter gene construct comprises a transcriptional regulatory sequence and a reporter gene that is functionally bound to downstream of the transcriptional regulatory sequence. The reporter gene construct is activated dependently of environment and the reporter gene codes for a protein producible of producing a free radical by the activation of the transcriptional regulatory sequence.

16 Claims, 9 Drawing Sheets

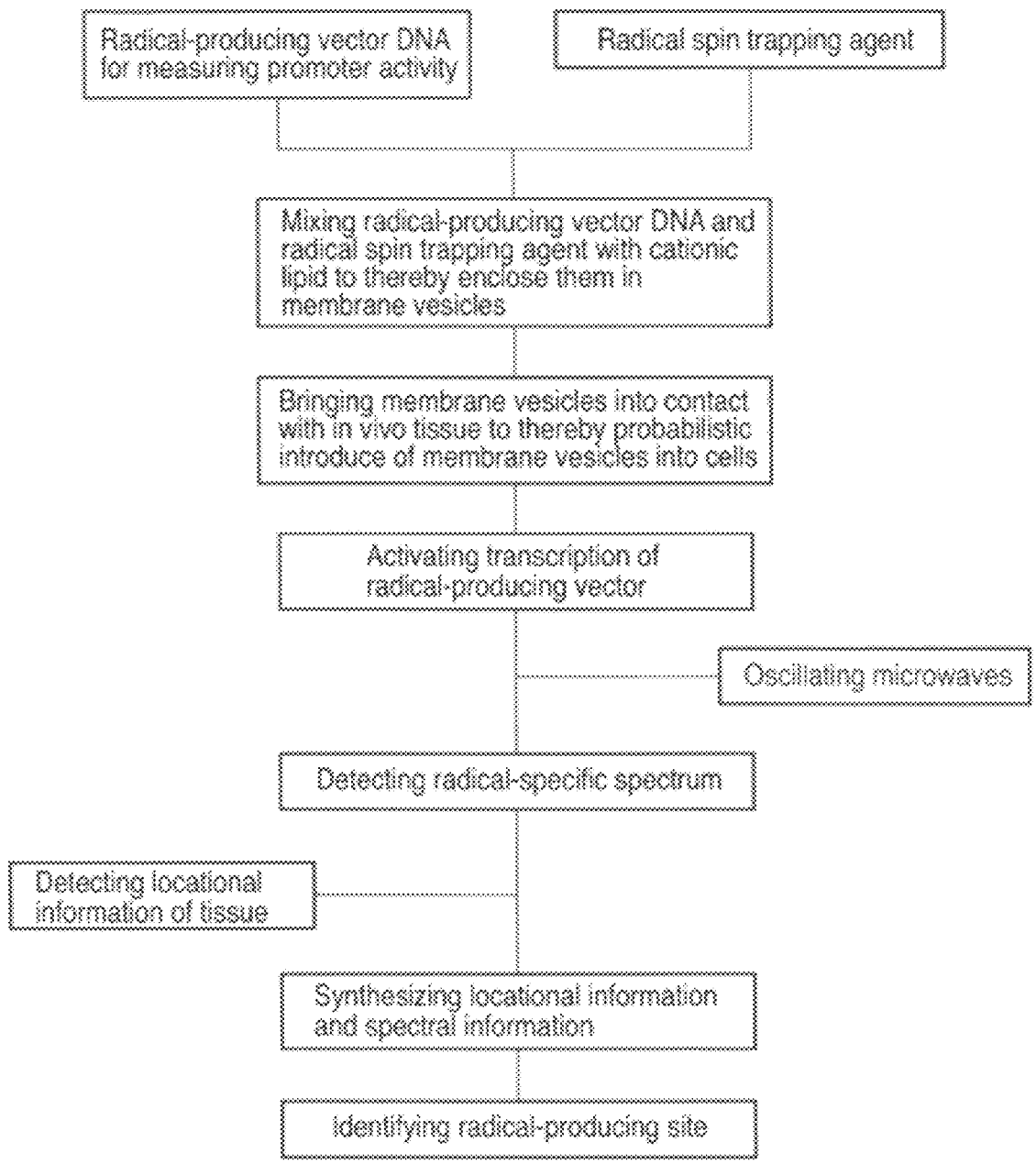
F I G. 8

US 8,546,079 B2

SEQUENCE LISTING

<160> NUMBER OF SEQ ID NOS: 7

<210> SEQ ID NO 1
<211> LENGTH: 4112
<212> TYPE: DNA
<213> ORGANISM: Artificial Sequence
<220> FEATURE:
<223> OTHER INFORMATION: iNOS cDNA (wild type)

<400> SEQUENCE: 1

```
gggacacagt gtcactggtt tgaaacttct cagccacctt ggtgaaggga ctgagctgtt      60
agagacactt ctgaggctcc tcacgcttgg gtcttgttca ctccacggag tagcctagtc     120
aactgcaaga gaacggagaa cggagaacgg agaacgttgg atttggagca gaagtgcaaa    180
gtctcagaca tggcttgccc ctggaagttt ctcttcaaag tcaaatccta ccaaagtgac    240
ctgaaagagg aaaaggacat taacaacaac gtgaagaaaa ccccttgtgc tgttctcagc    300
ccaacaatac aagatgaccc taagagtcac caaaatggct ccccgcagct cctcactggg    360
acagcacaga atgttccaga atccctggac aagctgcacg tgactccatc gacccgtcca    420
cagtatgtga ggatcaaaaa ctggggcagt ggagagattt tgcatgacac tcttcaccac    480
aaggccacat cggatttcac ttgcaagtcc aagtcttgct tggggtccat catgaacccc    540
aagagtttga ccagaggacc cagagacaag cctacccctc tggaggagct cctgcctcat    600
gccattgagt tcatcaacca gtattatggc tcctttaaag aggcaaaaat agaggaacat    660
ctggccaggc tggaagctgt aacaaaggaa atagaaacaa caggaaccta ccagctcact    720
ctggatgagc tcatctttgc caccaagatg gcctggagga atgcccctcg ctgcatcggc    780
aggatccagt ggtccaacct gcaggtcttt gacgctcgga actgtagcac agcacaggaa    840
atgtttcagc acatctgcag acacatactt tatgccacca caatggcaa catcaggtcg    900 gccatcactg tgttccccca gcggactgac ggcaaacatg acttcaggct ctggaattca    960
cagctcatcc ggtacgctgg ctaccagatg cccgatggca ccatcagagg ggatgctgcc    1020
accttggagt tcacccagtt gtgcatcgac ctaggctgga gcccgcta tggccgcttt    1080 gatgtgctgc ctctggtctt gcaagctgat ggtcaagatc cagaggtctt tgaaatccct    1140
cctgatcttg tgttggaggt gaccatggag catcccaagt acgagtggtt ccaggagctc    1200
gggttgaagt ggtatgcact gcctgccgtg gccaacatgc tactggaggt gggtggcctc    1260
gaattcccag cctgcccctt caatggttgg tacatgggca ccgagattgg agttcgagac    1320
ttctgtgaca cacagcgcta caacatcctg gaggaagtgg gccgaaggat gggcctggag    1380
acccacacac tggcctccct ctggaaagac cgggctgtca cggagatcaa tgtggctgtg    1440
```

```
ctccatagtt tccagaagca gaatgtgacc atcatggacc accacacagc ctcagagtcc   1500
ttcatgaagc acatgcagaa tgagtaccgg gcccgtggag gctgcccggc agactggatt   1560
tggctggtcc ctccagtgtc tgggagcatc acccctgtgt tccaccagga gatgttgaac   1620
tatgtcctat ctccattcta ctactaccag atcgagccct ggaagaccca catctggcag   1680
aatgagaagc tgaggcccag gaggagagag atccgattta gagtcttggt gaaagtggtg   1740
ttctttgctt ccatgctaat gcgaaaggtc atggcttcac gggtcagagc cacagtcctc   1800
tttgctactg agacagggaa gtctgaagca ctagccaggg acctggccac cttgttcagc   1860
tacgccttca acaccaaggt tgtctgcatg gaccagtata aggcaagcac cttggaagag   1920
gagcaactac tgctggtggt gacaagcaca tttgggaatg agactgtcc cagcaatggg    1980 cagactctga agaaatctct gttcatgctt agagaactca accacacctt caggtatgct   2040
gtgtttggcc ttggctccag catgtaccct cagttctgcg cctttgctca tgacatcgac   2100
cagaagctgt cccacctggg agcctctcag cttgccccaa caggagaagg ggacgaactc   2160
agtgggcagg aggatgcctt ccgcagctgg gctgtacaaa ccttccgggc agcctgtgag   2220 accttttgatg tccgaagcaa acatcacatt cagatcccga aacgcttcac ttccaatgca   2280
acatgggagc cacagcaata taggctcatc cagagcccgg agcctttaga cctcaacaga   2340
gccctcagca gcatccatgc aaagaatgtg tttaccatga ggctgaaatc ccagcagaat   2400
ctgcagagtg aaaagtccag ccgcaccacc ctcctcgttc agctcacctt cgagggcagc   2460
cgagggccca gctacctgcc tggggaacac ctggggatct tcccaggcaa ccagaccgcc   2520
ctggtgcagg gaatcttgga gcgagttgtg gattgtccta ccacacacca aactgtgtgc   2580
ctggaggttc tggatgagag cggcagctac tgggtcaaag acaagaggct gcccccctgc   2640
tcactcagcc aagccctcac ctacttcctg gacattacga cccctcccac ccagctgcag   2700
ctccacaagc tggctcgctt tgccacggac gagacggata ggcagagatt ggaggccttg   2760
tgtcagccct cagagtacaa tgactggaag ttcagcaaca accccacgtt cctggaggtg   2820
cttgaagagt tccctttcctt gcatgtgccc gctgccttcc tgctgtcgca gctccctatc   2880
ttgaagcccc gctactactc catcagctcc tcccaggacc acacccctct ggaggttcac   2940
ctcactgtgg ccgtggtcac ctaccgcacc cgagatggtc agggtcccct gcaccatgga   3000
gtctgcagca cttggatcag gaacctgaag ccccaggacc cagtgccctg ctttgtgcga   3060
agtgtcagtg gcttccagct ccctgaggac ccctcccagc cttgcatcct cattgggcct   3120
ggtacgggca ttgctccctt ccgaagtttc tggcagcagc ggctccatga ctcccagcac   3180
aaagggctca aggaggccg catgagcttg tgtttgggt gccggcaccc ggaggaggac   3240
cacctctatc aggaagaaat gcaggagatg gtccgcaaga gagtgctgtt ccaggtcac    3300 acaggctact cccggctgcc cggcaaaccc aaggtctacg ttcaggacat cctgcaaaag   3360
cagctggcca atgaggtact cagcgtgctc acggggagc agggccacct ctacgtttgc   3420
ggagatgtgc gcatggctcg ggatgtggct accacgttga agaagctggt ggccaccaag   3480
ctgaacttga gcgaggagca ggtggaagac tatttcttcc agctcaagag ccagaaacgt   3540
tatcatgaag atatcttcgg tgcagtcttt tcctatgggg caaaaagggg cagcgccttg   3600
gaggagccca aagccacgag gctctgacag cccagagttc cagcttctgg cactgagtaa   3660
agataatggt gaggggcttg gggagacagc gaaatgcaat ccccccaag cccctcatgt    3720 cattccccc tcctccaccc taccaagtag tattgtacta ttgtggacta ctaaatctct    3780
ctcctctcct ccctcccctc tctccctttc ctcccttctt ctccactccc cagctccctc   3840
```

```
cttctcctcc tcctcctttg cctctcactc ttccttggag ctgagagcag agaaaaactc    3900
aacctcctga ctgaagcact tgggtgacc accaggaggc accatgccac cgctctaata    3960
cttagctgca ctatgtacag atatttatac ttcatattta agaaaacaga tacttttgtc    4020
tactcccaat gatggcttgg gcctttcctg tataattcct tgatgaaaaa tatttatata    4080
aaatacattt tattttaaaa aaaaaaaaaa aa                                  4112
```

<210> SEQ ID NO 2
<211> LENGTH: 3375
<212> TYPE: DNA
<213> ORGANISM: Artificial Sequence
<220> FEATURE:
<223> OTHER INFORMATION: iNOS mutant (C-terminal 21 aa truncated)

<400> SEQUENCE: 2

```
atggcttgcc cctggaagtt tctcttcaaa gtcaaatcct accaaagtga cctgaaagag      60
gaaaaggaca ttaacaacaa cgtgaagaaa accccttgtg ctgttctcag cccaacaata     120
caagatgacc ctaagagtca ccaaaatggc tccccgcagc tcctcactgg gacagcacag     180
aatgttccag aatccctgga caagctgcac gtgactccat cgacccgtcc acagtatgtg     240
aggatcaaaa actggggcag tggagagatt ttgcatgaca ctcttcacca aaggccaca      300 tcggatttca cttgcaagtc caagtcttgc ttggggtcca tcatgaaccc caagagtttg     360
accagaggac ccagagacaa gcctacccct ctggaggagc tcctgcctca tgccattgag     420
ttcatcaacc agtattatgg ctccttaaa gaggcaaaaa tagaggaaca tctggccagg     480
ctggaagctg taacaaagga aatagaaaca acaggaacct accagctcac tctggatgag     540
ctcatctttg ccaccaagat ggcctggagg aatgccctc gctgcatcgg caggatccag     600
tggtccaacc tgcaggtctt tgacgctcgg aactgtagca cagcacagga aatgtttcag     660
cacatctgca gacacatact ttatgccacc aacaatggca acatcaggtc ggccatcact     720
gtgttccccc agcggactga cggcaaacat gacttcaggc tctggaattc acagctcatc     780
cggtacgctg gctaccagat gcccgatggc accatcagag gggatgctgc acccttggag     840
ttcacccagt tgtgcatcga cctaggctgg aagccccgct atggccgctt tgatgtgctg     900
cctctggtct tgcaagctga tggtcaagat ccagaggtct ttgaaatccc tcctgatctt     960
gtgttggagg tgaccatgga gcatcccaag tacgagtggt tccaggagct cgggttgaag    1020
tggtatgcac tgcctgccgt ggccaacatg ctactggagg tgggtggcct cgaattccca    1080 gcctgccccct tcaatggttg gtacatgggc accgagattg agttcgaga cttctgtgac    1140 acacagcgct acaacatcct ggaggaagtg ggccgaagga tgggcctgga gacccacaca    1200
ctggcctccc tctggaaaga ccgggctgtc acggagatca atgtggctgt gctccatagt    1260
ttccagaagc agaatgtgac catcatggac caccacacag cctcagagtc cttcatgaag    1320
cacatgcaga atgagtaccg ggcccgtgga ggctgcccgg cagactggat ttggctggtc    1380
cctccagtgt ctgggagcat caccctgtg ttccaccagg agatgttgaa ctatgtccta    1440
tctccattct actactacca gatcgagccc tggaagaccc acatctggca gaatgagaag    1500
ctgaggccca ggaggagaga gatccgattt agagtcttgg tgaaagtggt gttctttgct    1560
tccatgctaa tgcgaaaggt catggcttca cgggtcagag ccacagtcct cttttgctact    1620 gagacaggga agtctgaagc actagccagg gacctggcca ccttgttcag ctacgccttc    1680
aacaccaagg ttgtctgcat ggaccagtat aaggcaagca ccttggaaga ggagcaacta    1740
ctgctggtgg tgacaagcac atttgggaat ggagactgtc ccagcaatgg gcagactctg    1800
```

```
aagaaatctc tgttcatgct tagagaactc aaccacacct tcaggtatgc tgtgtttggc    1860
cttggctcca gcatgtaccc tcagttctgc gcctttgctc atgacatcga ccagaagctg    1920
tcccacctgg gagcctctca gcttgcccca acaggagaag gggacgaact cagtgggcag    1980
gaggatgcct tccgcagctg ggctgtacaa accttccggg cagcctgtga gacctttgat    2040
gtccgaagca acatcacat tcagatcccg aaacgcttca cttccaatgc aacatgggag    2100
ccacagcaat ataggctcat ccagagcccg gagcctttag acctcaacag agccctcagc    2160
agcatccatg caaagaatgt gtttaccatg aggctgaaat cccagcagaa tctgcagagt    2220
gaaaagtcca gccgcaccac cctcctcgtt cagctcacct tcgagggcag ccgagggccc    2280
agctacctgc ctggggaaca cctggggatc ttcccaggca accagaccgc cctggtgcag    2340
ggaatcttgg agcgagttgt ggattgtcct acaccacacc aaactgtgtg cctggaggtt    2400
ctggatgaga gcggcagcta ctgggtcaaa gacaagaggc tgccccctg ctcactcagc    2460 caagccctca cctacttcct ggacattacg acccctccca cccagctgca gctccacaag    2520
ctggctcgct ttgccacgga cgagacggat aggcagagat tggaggcctt tgtgtcagccc   2580 tcagagtaca atgactggaa gttcagcaac aaccccacgt tcctggaggt gcttgaagag    2640
ttcccttcct tgcatgtgcc cgctgccttc ctgctgtcgc agctccctat cttgaagccc    2700
cgctactact ccatcagctc ctcccaggac acaccccct cggaggttca cctcactgtg    2760
gccgtggtca cctaccgcac ccgagatggt cagggtcccc tgcaccatgg agtctgcagc    2820
acttggatca ggaacctgaa gcccaggac ccagtgccct gctttgtgcg aagtgtcagt    2880
ggcttccagc tccctgagga ccccctcccag ccttgcatcc tcattgggcc tggtacgggc    2940
attgctccct tccgaagttt ctggcagcag cggctccatg actcccagca caaagggctc    3000
aaaggaggcc gcatgagctt ggtgtttggg tgccggcacc cggaggagga ccacctctat    3060
caggaagaaa tgcaggagat ggtccgcaag agagtgctgt tccaggtgca cacaggctac    3120 tccccggctgc ccggcaaacc caaggtctac gttcaggaca tcctgcaaaa gcagctggcc    3180
aatgaggtac tcagcgtgct ccacggggag cagggccacc tctacgtttg cggagatgtg    3240
cgcatggctc gggatgtggc taccacgttg aagaagctgg tggccaccaa gctgaacttg    3300
agcgaggagc aggtggaaga ctatttcttc cagctcaaga gccagaaacg ttatcatgaa    3360
gatatcttcg gttga                                                     3375
```

<210> SEQ ID NO 3
<211> LENGTH: 3531
<212> TYPE: DNA
<213> ORGANISM: Artificial Sequence
<220> FEATURE:
<223> OTHER INFORMATION: iNOS mutant (C-terminal 31 aa fused to V5-His tag)

<400> SEQUENCE: 3

```
atggcttgcc cctggaagtt tctcttcaaa gtcaaatcct accaaagtga cctgaaagag      60
gaaaaggaca ttaacaacaa cgtgaagaaa acccccttgtg ctgttctcag cccaacaata     120
caagatgacc ctaagagtca ccaaaatggc tccccgcagc cctcactgg acagcacag       180 aatgttccag aatccctgga caagctgcac gtgactccat cgacccgtcc acagtatgtg     240
aggatcaaaa actgggcag tggagagatt ttgcatgaca ctcttcacca aaggccaca      300 tcggatttca cttgcaagtc caagtcttgc ttggggtcca tcatgaaccc caagagtttg     360
accagaggac ccagagacaa gcctacccct ctggaggagc cctgcctca tgccattgag      420 ttcatcaacc agtattatgg ctcctttaaa gaggcaaaaa tagaggaaca tctggccagg     480
```

```
ctggaagctg taacaaagga aatagaaaca acaggaacct accagctcac tctggatgag    540
ctcatctttg ccaccaagat ggcctggagg aatgcccctc gctgcatcgg caggatccag    600
tggtccaacc tgcaggtctt tgacgctcgg aactgtagca cagcacagga aatgtttcag    660
cacatctgca gacacatact ttatgccacc aacaatggca acatcaggtc ggccatcact    720
gtgttccccc agcggactga cggcaaacat gacttcaggc tctggaattc acagctcatc    780
cggtacgctg gctaccagat gcccgatggc accatcagag gggatgctgc caccttggag    840
ttcacccagt tgtgcatcga cctaggctgg aagccccgct atggccgctt tgatgtgctg    900
cctctggtct tgcaagctga tggtcaagat ccagaggtct ttgaaatccc tcctgatctt    960
gtgttggagg tgaccatgga gcatcccaag tacgagtggt tccaggagct cgggttgaag   1020
tggtatgcac tgcctgccgt ggccaacatg ctactggagg tgggtggcct cgaattccca   1080
gcctgcccct tcaatggttg gtacatgggc accgagattg agttcgaga  cttctgtgac   1140 acacagcgct acaacatcct ggaggaagtg ggccgaagga tgggcctgga gacccacaca   1200
ctggcctccc tctggaaaga ccgggctgtc acggagatca atgtggctgt gctccatagt   1260
ttccagaagc agaatgtgac catcatggac caccacacag cctcagagtc cttcatgaag   1320
cacatgcaga atgagtaccg ggcccgtgga ggctgcccgg cagactggat ttggctggtc   1380
cctccagtgt ctgggagcat caccectgtg ttccaccagg agatgttgaa ctatgtccta   1440
tctccattct actactacca gatcgagccc tggaagaccc acatctggca gaatgagaag   1500
ctgaggccca ggaggagaga gatccgattt agagtcttgg tgaaagtggt gttcttttgct   1560 tccatgctaa tgcgaaaggt catggcttca cgggtcagag ccacagtcct ctttgctact   1620
gagacaggga agtctgaagc actagccagg gacctggcca ccttgttcag ctacgccttc   1680
aacaccaagg ttgtctgcat ggaccagtat aaggcaagca ccttggaaga ggagcaacta   1740
ctgctggtgg tgacaagcac atttgggaat ggagactgtc ccagcaatgg gcagactctg   1800
aagaaatctc tgttcatgct tagagaactc aaccacacct tcaggtatgc tgtgtttggc   1860
cttggctcca gcatgtaccc tcagttctgc gcctttgctc atgacatcga ccagaagctg   1920
tcccacctgg gagcctctca gcttgcccca acaggagaag gggacgaact cagtgggcag   1980
gaggatgcct tccgcagctg ggctgtacaa accttccggg cagcctgtga gaccctttgat   2040 gtccgaagca acatcacat  tcagatcccg aaacgcttca cttccaatgc aacatgggag   2100
ccacagcaat ataggctcat ccagagcccg gagcctttag acctcaacag agccctcagc   2160
agcatccatg caaagaatgt gtttaccatg aggctgaaat cccagcagaa tctgcagagt   2220
gaaaagtcca gccgcaccac cctcctcgtt cagctcacct tcgagggcag ccgagggccc   2280
agctacctgc ctggggaaca cctggggatc ttcccaggca accagaccgc cctggtgcag   2340
ggaatcttgg agcgagttgt ggattgtcct acaccacacc aaactgtgtg cctggaggtt   2400
ctggatgaga gcggcagcta ctgggtcaaa gacaagaggc tgccccctg ctcactcagc   2460 caagccctca cctacttcct ggacattacg accctcccaa cccagctgca gctccacaag   2520
ctggctcgct tgccacggga cgagacggat aggcagagat ggaggccctt gtgtcagccc   2580
tcagagtaca atgactggaa gttcagcaac aaccccacgt tcctggaggt gcttgaagag   2640
```

```
ttcccttcct tgcatgtgcc cgctgccttc ctgctgtcgc agctccctat cttgaagccc    2700
cgctactact ccatcagctc ctcccaggac cacaccccct cggaggttca cctcactgtg    2760
gccgtggtca cctaccgcac ccgagatggt cagggtcccc tgcaccatgg agtctgcagc    2820
acttggatca ggaacctgaa gccccaggac ccagtgccct gctttgtgcg aagtgtcagt    2880
ggcttccagc tccctgagga ccccteccag ccttgcatcc tcattgggcc tggtacgggc    2940
attgctccct tccgaagttt ctggcagcag cggctccatg actcccagca caaagggctc    3000
aaaggaggcc gcatgagctt ggtgtttggg tgccggcacc cggaggagga ccacctctat    3060
caggaagaaa tgcaggagat ggtccgcaag agagtgctgt tccaggtgca cacaggctac    3120
tcccggctgc ccggcaaacc caaggtctac gttcaggaca tcctgcaaaa gcagctggcc    3180
aatgaggtac tcagcgtgct ccacggggag cagggccacc tctacgtttg cggagatgtg    3240
cgcatggctc gggatgtggc taccacgttg aagaagctgg tggccaccaa gctgaacttg    3300
agcgaggagc aggtggaaga ctatttcttc cagctcaaga gccagaaacg ttatcatgaa    3360
gatatcttcg gtgcagtctt ttcctatggg gcaaaaaagg gcagcgcctt ggaggagccc    3420
aaagccacga ggctcggtct agagggcccg cggttcgaag gtaagcctat ccctaaccct    3480
ctcctcggtc tcgattctac gcgtaccggt catcatcacc atcaccattg a             3531

<210> SEQ ID NO 4
<211> LENGTH: 329
<212> TYPE: DNA
<213> ORGANISM: Artificial Sequence
<220> FEATURE:
<223> OTHER INFORMATION: CYP1A1 enhancer

<400> SEQUENCE: 4
ttaagagcct cacccacggt tccctcccc cagctagcgt gacagcactg ggacccgcgc      60
ccggttgtga gttgggtagc tgggtggctg cgcgggcctc caggctcttc tcacgcaact    120
ccggggcacc ttgtccccag ccaggtgggg cggagacagg cagcccgacc tctgccccca    180
gaggatggag caggcttacg cacgctagcc tcaggaacct gtgtgcgtgc caagcatcac    240
cctttgtagc cccagacccc ctcctgctgt ctcgcgtgga tccttcctcc acccttttcct   300 ccaccatact tagatagctc tgcacccgc                                       329

<210> SEQ ID NO 5
<211> LENGTH: 23
<212> TYPE: DNA
<213> ORGANISM: Artificial Sequence
<220> FEATURE:
<223> OTHER INFORMATION: forward primer

<400> SEQUENCE: 5
ggcagagatt ggaggccttg tgt                                             23

<210> SEQ ID NO 6
<211> LENGTH: 30
<212> TYPE: DNA
<213> ORGANISM: Artificial Sequence
<220> FEATURE:
<223> OTHER INFORMATION: reverse primer 1

<400> SEQUENCE: 6
aggtctagat tcaaccgaag atatcttcat                                      30

<210> SEQ ID NO 7
<211> LENGTH: 32
<212> TYPE: DNA
```

```
<213> ORGANISM: Artificial Sequence
<220> FEATURE:
<223> OTHER INFORMATION: reverse primer 2

<400> SEQUENCE: 7
ctctgtctag accgagcctc gtggctttgg gc                                    32
```

REPORTER GENE CONSTRUCT, ASSAY KIT AND DETECTION METHOD

CROSS-REFERENCE TO RELATED APPLICATIONS

This application is based upon and claims the benefit of priority from Japanese Patent Application No. 2010-214480, filed Sep. 24, 2010; the entire contents of which are incorporated herein by reference.

FIELD

Embodiments described herein relate generally to a reporter gene construct, an assay kit and a detection method.

BACKGROUND

Now, disease genes that target disease-specific genomic structure abnormalities have been identified, and accordingly, a multiplicity of genes associated with diseases, such as cancer, have been found. These are attracting attention as a diagnostic biomarker for diseases. As the expression of a biomarker cannot always satisfactorily be realized at an early date of disease development, the diagnosis by the detection of a biomarker is not always appropriate as an early diagnosis.

The early diagnosis is absolutely necessary from the viewpoint of improvement in cure rate and relieving the burden on patients. As an approach therefor, it is contemplated to observe an early change of disease development by detecting an abnormality of genomic modification and, accompanying the same, a change of promoter activity.

The change of promoter activity regulates the probability of gene expression, and is observed earlier than the expression of disease-associated gene and disease-associated protein.

A reporter gene assay is available as a method of detecting the condition of activation of a particular promoter within a cell. The reporter gene assay is a method comprising linking a reporter gene for visualizing the promoter activity, such as GFP, β-galactosidase or luciferase gene, downstream of a promoter of interest to thereby obtain a reporter construct, introducing the reporter construct in a test cell, and quantifying the condition of promoter activation on the basis of the activity of expressed reporter protein. The reporter gene assay, as a method of quantifying a cellular promoter activity, is mainly used in in-vitro diagnosis. Performing in vivo the reporter gene assay in a non-invasive manner is being tested in animal experiments. However, such tests all use optical detection methods. Therefore, they pose, for example, the problem that the luminescence and/or fluorescence in a deep area (approximately 2 cm or more) of the body is attenuated, so that the scope of application of the reporter gene assay is limited to a shallow part of the body and the like.

BRIEF DESCRIPTION OF THE DRAWINGS

FIG. 8 is a flow chart showing the procedure of a cellular detection method by an electron spin resonance method using the production of NO as an indication according to still a further embodiment.

DETAILED DESCRIPTION

Figure 1:
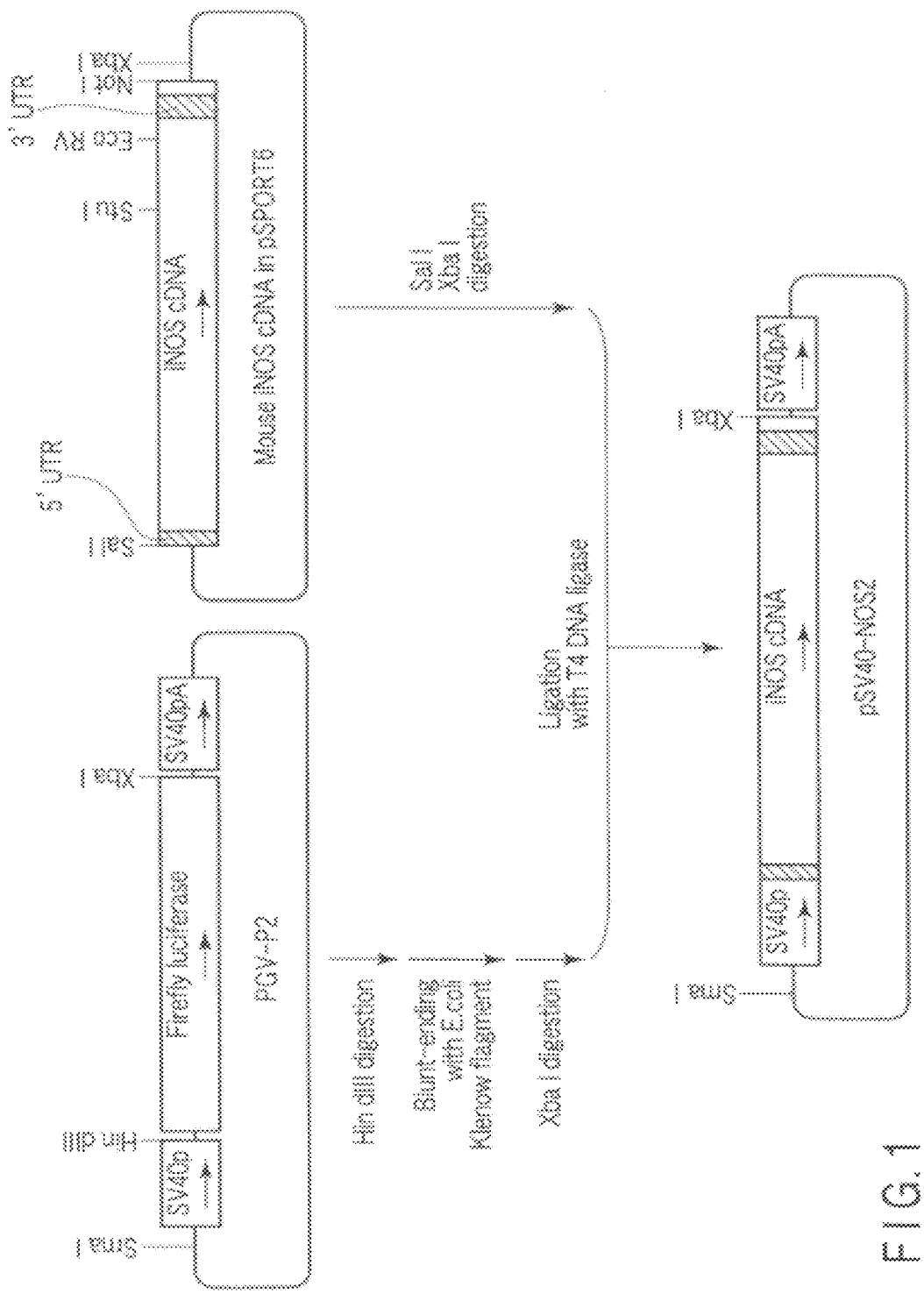
FIG. 1 is a view showing pSV40-NOS2 as a form of vector according to one embodiment.

In general, according to one embodiment, there is provided novel means for detecting a change of transcription activity by using an electron spin resonance method.

According to one embodiment, there is provided a reporter gene construct comprising; a transcriptional regulatory sequence that is activated dependently of environment; and a reporter gene that is functionally bound to downstream of the transcriptional regulatory sequence, and that codes for a protein capable of producing a free radical by the activation of the transcriptional regulatory sequence; wherein the reporter gene construct is expressible in a cell.

According to another embodiment, there is provided a method of predicting an environment of a cell, comprising:

(1) introducing the reporter gene construct of claim 1 in a cell, (2) detecting any free radical produced by the cell obtained in (1), and (3) judging the environment of the cell on the basis of results obtained in (2) and then predicting the environment of the cell.

According to a further embodiment, there is provided a method of detecting a particular cell in a cell assembly, comprising:

(1) introducing the reporter gene construct of claim 1 in a cell assembly, (2) detecting any free radical produced in the cell assembly obtained in (1), (3) judging a cell having produced a free radical on the basis of results obtained in (2).

According to still a further embodiment, there is provided an assay kit for performing a method of assaying the environment of a cell or a method of detecting a particular cell, comprising:

(a) a reporter gene construct comprising;

a transcriptional regulatory sequence that is activated dependently of environment; and a reporter gene that is functionally bound to downstream of the transcriptional regulatory sequence, and that codes for a protein capable of producing a free radical by the activation of the transcriptional regulatory sequence, wherein the reporter gene construct is expressible in a cell, and (b) a spin trapping agent.

The reporter gene construct comprising a transcriptional regulatory sequence that is activated dependently of environment and, functionally bound to downstream thereof, a reporter gene that codes for a protein capable of producing a free radical by the activation of the transcriptional regulatory sequence according to one aspect is delivered into a cell, and produces a free radical dependently of the environment of the cell. Therefore, whether or not the transcriptional regulatory sequence is activated is judged using the production or non-production of a free radical or the amount of free radical produced as an indication, and on the basis of the judgment, the environment of the cell in which the reporter gene construct has been introduced and the state of the cell can be predicted.

The term "environment" used herein means the various states of a cell into which the delivery of the reporter gene construct is intended, for example, a pathological state of cell, such as a cancerized state, a state of being exposed to a hazardous substance and a state of being exposed to a low-oxygen environment, a low-temperature environment or a high-temperature environment.

The expression "activated dependently of environment" means that an intended cell is activated when it lies in an intended environment.

The term "transcriptional regulatory sequence" refers to any sequence that regulates the transcription of a gene located downstream of the sequence. For example, the transcriptional regulatory sequence may be the enhancer and/or promoter (hereinafter referred to as enhancer/promoter) of a particular gene. The "particular gene" may be any gene that is activated dependently of environment.

The expression "functionally bound" used herein means that binding is performed in such a condition that an intended working capability is maintained or that an intended working capability can be exercised.

The "protein capable of producing a free radical" refers to any protein that produces a free radical, such as nitrogen monoxide (NO.), superoxide ($O_2^-$.) or hydroxy radical (OH.), under the activation of the transcriptional regulatory sequence activated dependently of environment. For example, the protein may be an enzyme that acts on a substrate, thereby producing a free radical.

The "reporter gene coding for a protein capable of producing a free radical" may be any of a gene coding for the above protein, a gene containing a sequence coding for the above protein, a gene containing the part of the protein capable of producing a free radical and a gene coding for the above protein in which a mutation, such as substitution, deletion and/or addition, is contained within a range capable of producing a free radical.

The reporter gene construct is not limited as long as it can be delivered to an intended cell and is capable of expressing a reporter gene in a target environment. The reporter gene construct may be introduced in a cell through any means which is in itself publicly known. For example, the introduction of the reporter gene construct may be performed by a method using a cationic lipid (lipofection) or a physicochemical means using electroporation, ultrasonic waves, magnetism or a particle gun. The reporter gene construct itself may be constructed as an adenovirus or other virus vector or a plasmid vector. The reporter gene construct itself may be constructed in the form of a carrier, for example, an ion complex carrier, such as a cationic lipid, a basic polymer, a synthetic polypeptide or apatite carbonate.

In one embodiment, the reporter gene construct may be a vector capable of detecting a promoter activity. Such a vector may contain a DNA comprising, linked together, an enhancer/promoter of a particular gene, a gene coding for a protein capable of producing a free radical and a poly(A) addition signal. The enhancer/promoter of a particular gene may comprise an enhancer of a particular gene and an arbitrary promoter. In this embodiment, the enhancer is a specific nucleotide sequence to which a transcription factor activated by a substrate is bound, the base sequence being capable of activating the transcription of a downstream gene through the ligation of the transcription factor. The promoter is a nucleotide sequence absolutely necessary for the initiation of gene transcription, in which an RNA polymerase binding sequence is contained.

[Transcriptional Regulatory Sequence]

The transcriptional regulatory sequence may be, for example, an enhancer and/or a promoter. The transcriptional regulatory sequence activated dependently of environment may be an enhancer/promoter of a particular gene. The term "particular gene" used herein means is not limited as long as it is a gene activated dependently of environment, and may be an enhancer/promoter specifically activated in a particular state of each cell as an assay object. As the state of an assay object cell, there can be mentioned a state of cancerized cell, a state of cell exposed to a hazardous substance, a state of cell exposed to a low-oxygen environment, a low-temperature environment or a high-temperature environment, or the like. For example, the transcriptional regulatory sequence may be a gene activated in a cell of particular disease condition, namely, an enhancer and/or promoter of disease-associated gene. An example of the enhancer and/or promoter of disease-associated gene is an enhancer/promoter activated in the state of a cancerized cell. As such, there can be mentioned, for example, the enhancer/promoter of a myc gene, a fos gene or a ras gene. Further, as the enhancer/promoter activated in the state of a cell exposed to a hazardous substance, there can be mentioned, for example, the enhancer/promoter of a drug-metabolism-associated enzyme gene group, including cytochrome 1A1 gene. With respect to the enhancer/promoter of each of these genes, it is practicable to separate only an enhancer sequence and use the enhancer sequence in a form connected to an arbitrary promoter. As the arbitrary promoter, use can be made of, for example, the minimum promoter of cytomegalovirus (CMV), the early promoter of simian virus 40 (SV40) or the thymidine kinase promoter of herpes simplex virus. However, the arbitrary promoter useful in carrying out this embodiment is not limited to these, and those with altered gene sequences can be used as long as the function as the promoter is not deteriorated.

For example, use can be made of a reporter gene construct wherein the transcriptional regulatory sequence is a promoter sequence selected from the group consisting of cytomegalovirus immediate promoter, simian virus 40 early promoter and herpes simplex virus thymidine kinase, and wherein the insertion site of the enhancer of a gene activated dependently of environment is further provided upstream of the promoter sequence. Before the use of such a construct, it is appropriate to further incorporate an enhancer of a particular gene, for example, an enhancer of a disease-associated gene in the insertion site of the enhancer.

[Reporter Gene]

As an example of the gene coding for a protein capable of producing a free radical for use as the reporter gene, there can be mentioned a gene group coding for nitrogen monoxide synthase (NOS, NO Synthase) capable of synthesizing nitrogen monoxide (NO.) from L-arginine, a gene coding for xanthine oxidase (XO, Xanthine Oxidase) capable of generating superoxide ($O_2^-$.) in the process of oxidation of hypoxanthine to xanthine, or the like. However, the reporter gene is not limited to these genes, and other genes may be used as long as they are genes coding for proteins having the activity of producing a free radical.

An example in which a NOS gene is used will be mentioned below. Generally, three types of NOS genes, namely, iNOS (inducible NOS), nNOS (neural NOS) and eNOS (endothelial NOS) are recognized in mammals. All these NOS genes can be used in this embodiment. Among these NOS genes, nNOS and eNOS are constitutively expressed inside cells, and the enzymatic activity thereof (activity of NO. synthesis) is regulated by an intracellular calcium concentration. In this embodiment, although wild-type nNOS and eNOS genes can be used, it is preferred to use mutant-type nNOS and eNOS genes in which a mutation ensuring the freedom from the regulation by the intracellular calcium concentration has been introduced. In contrast, iNOS is derived on a transcription level by inflammatory cytokine (TNF-α, IL-1β, IFN-γ, etc.), and the enzymatic activity thereof is not regulated by an intracellular calcium concentration. Therefore, in the case of iNOS, a wild-type gene can be preferably used. However, the use of iNOS gene in this embodiment is not limited to the use of a wild-type gene. For example, use may be made of a mutant-type iNOS gene having enhanced the capability of producing a free radical. Also, for example, use may be made of a mutant-type iNOS gene having enhanced the activity of NO. synthesis and a mutant-type iNOS gene having realized a constitutive enzyme activation. The origin of three types of NOS genes in this embodiment is not limited as long as it is a mammal. Moreover, cNOS (constitutive NOS) which is constitutively present as a category of NOS genes may also be used in this embodiment.

[Transcription Terminator Gene]

The reporter gene construct of the invention may further contain a transcription terminator gene downstream of the reporter gene. The transcription terminator gene is not limited as long as it is a gene capable of terminating the transcription of the upstream gene. It may be, for example, a poly(A) addition signal.

The poly(A) addition signal is not limited as long as it functions for terminating the transcription of a mammalian gene. As examples thereof, there can be mentioned, for example, a late poly(A) addition signal of SV 40 virus, a poly(A) addition signal of bovine growth hormone gene, and the like. However, the poly(A) addition signal useful in carrying out this embodiment is not limited to these, and one with an altered gene sequence may be used as long as the function as the poly(A) addition signal is not deteriorated.

[Construction of Radical-Producing Vector]

A form of vector according to one embodiment will be described below. This vector is a form of vector using an iNOS gene as a gene for free radical production.

The DNA sequence of mouse iNOS gene is shown in SEQ ID NO: 1. The origin of the iNOS gene is not limited as long as it is a mammal, and the iNOS gene is in no way limited to the iNOS gene derived from a mouse. For example, the iNOS gene may be one derived from a human, a monkey, a rat, etc. It is not necessary for the DNA sequence of the iNOS gene to completely homologous to the DNA sequence of SEQ ID NO: 1 as long as the enzymatic activity (activity of NO. synthesis) thereof is not lost. The iNOS gene may be one acquired by known genetic engineering techniques. For example, the iNOS gene may be acquired by amplification by means of PCR using a primer set specific to the base sequence. Alternatively, the entirety of the base sequence thereof may be artificially synthesized. Also, use may be made of the iNOS gene already incorporated in the vector.

The iNOS gene used in this embodiment may be a mutant-type gene. The DNA sequences of iNOS mutant-type genes are given in SEQ ID NO: 2 and SEQ ID NO: 3. The mutant-type genes code respectively for an iNOS protein having carboxy-terminal 21 amino acids deleted and an iNOS protein having 31 amino acids fused to the carboxy terminal. The mutant genes of SEQ ID NO: 2 and SEQ ID NO: 3 are derived from a mouse. However, the origin is not limited to a mouse, and genes from mammals, for example, a human, a monkey and a rat may be appropriately used. Further, the site of mutation is not limited as long as the mutation is introduced in an appropriate site corresponding to the origin of gene. These iNOS mutant-type genes can be acquired by applying known genetic engineering techniques. For example, they can be amplified by PCR using a specific primer set having a mutation introduced therein. Alternatively, the entire base sequence of each of mutant genes may be artificially synthesized.

A vector can be constructed by ligating the enhancer/promoter of a particular gene 5' upstream of the above-mentioned iNOS gene and ligating a poly(A) addition signal 3' downstream of the iNOS gene. Referring to FIG. 1, pSV40-NOS2 is a form of vector having the iNOS gene incorporated therein. In this form, SV 40 early promoter is used as the arbitrary promoter and SV40 late poly(A) addition signal used as the poly(A) addition signal. The promoter and poly(A) addition signal are not limited to these. This vector may be constructed by incorporating the iNOS gene in a commercially available vector. The vector for assaying the state of a cell according to this embodiment can be constructed by incorporating the enhancer of a particular gene upstream of the promoter of this vector.

Figure 2:
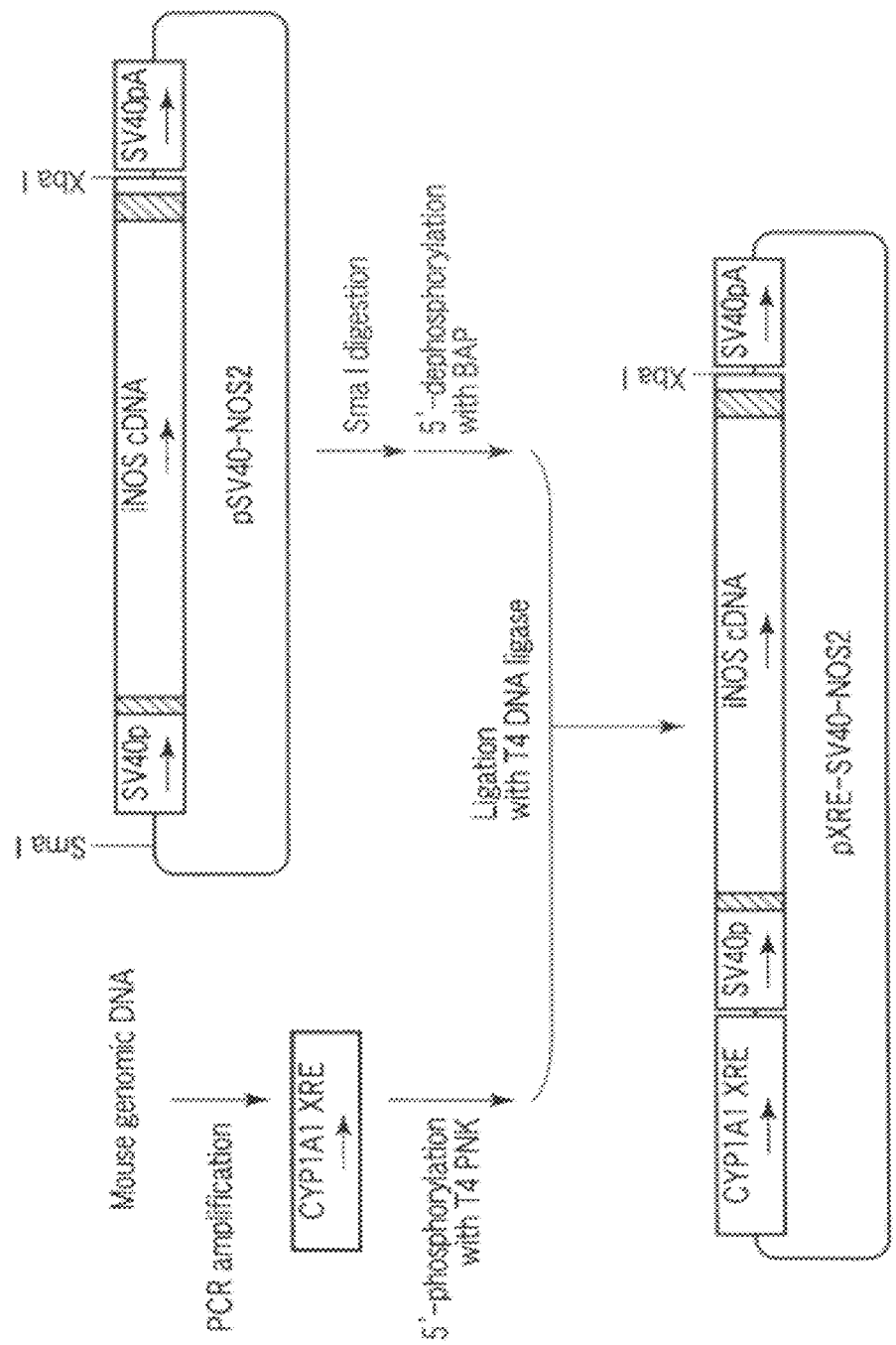
FIG. 2 is a view showing pXRE-SV40-NOS2 as a form of vector according to another embodiment.

Referring to FIG. 2, pXRE-SV40-NOS2 is a form of vector having an enhancer incorporated upstream of the promoter of the above vector. In this form, the enhancer of cytochrome 1A1 gene responsive to a carcinogen is incorporated as the enhancer. The DNA sequence of this enhancer is given in SEQ ID NO: 4. This enhancer can be acquired by applying known genetic engineering techniques. For example, the enhancer can be acquired by amplification by PCR using a primer set specific to the base sequence. The acquired enhancer can be incorporated in the vector by using known genetic engineering techniques.

Referring to FIG. 9, pCMV-iNOStr is a form of vector in which a mutant-type iNOS gene (SEQ ID NO: 2) having carboxy-terminal 21 amino acids deleted is incorporated. In this form, CMV promoter is used as the arbitrary promoter, and the poly(A) addition signal of bovine growth hormone gene used as the poly(A) addition signal. The promoter and poly(A) addition signal are not limited to these. This vector may be constructed by known genetic engineering techniques, for example, by preparing a mutant-type iNOS gene having its gene code altered through PCR or the like and incorporating the same in a commercially available vector. The vector for assaying the state of a cell according to this embodiment can be constructed by incorporating the enhancer of a particular gene upstream of the promoter of this vector.

Referring further to FIG. 9, pCMV-iNOS-F is a form of vector in which a mutant-type iNOS gene (SEQ ID NO: 3) having 31 amino acids fused to the carboxy terminal is incorporated. In this form, CMV promoter is used as the arbitrary promoter, and the poly(A) addition signal of bovine growth hormone gene used as the poly(A) addition signal. The promoter and poly(A) addition signal are not limited to these. In the mutant-type gene, a 31 amino acids sequence containing a V5-polyhistidine tag sequence is fused to the carboxy terminal. This vector may be constructed by known genetic engineering techniques, for example, by preparing a mutant-type iNOS gene having its gene code altered through PCR or the like and causing the same to form a fusion gene in combination with a V5-polyhistidine tag sequence incorporated in advance in a commercially available vector. As the commercially available vector for incorporating the mutant-type gene, there can be mentioned, for example, pcDNA4/V5-His vector or the like. In this form, the mutant-type iNOS gene having a 31 amino acids sequence containing a V5-polyhistidine tag sequence fused to the carboxy terminal was mentioned. However, as long as the activity of NO. synthesis of the mutant-type iNOS coded for by the mutant-type iNOS gene is increased, the sequence fused to the carboxy terminal may not be a V5-polyhistidine tag sequence, and the length of the fused amino acid sequence is not limited to 31 amino acids. The vector for assaying the state of a cell according to this embodiment can be constructed by incorporating the enhancer of a particular gene upstream of the promoter of this vector.

[Assaying the State of a Cell by Detecting a Free Radical Produced in Accordance with the Activity of the Transcriptional Regulatory Sequence]

In this embodiment, using a vector, the state of a cell is assayed by the production of a free radical.

In one mode of this embodiment, a method of assaying the state of a cell by producing nitrogen monoxide as a free radical with the use of a vector having the iNOS gene incorporated therein will be described below. First, the vector is introduced in a cell as an assay object and cultured for an arbitrary period of time. The cell as an assay object is preferably selected from among mammalian cells, such as those of a human, a monkey, a mouse and a rat.

In the introduction of the vector in a host cell, use may be made of any of known cell engineering techniques. As such techniques, there can be mentioned, for example, biochemical methods, such as a method using a cationic lipid (lipofection) and a method using calcium chloride. Further, there can be mentioned, for example, physicochemical methods, such as electroporation.

After the introduction of the vector in a host cell, the cell is cultured for an arbitrary period of time. During the culturing period, the cell as an assay object may be placed under conditions dependent of the state or environment of the cell. Under the conditions, the reporter gene construct is exposed to environmental stimulus. Simultaneously therewith or separately therefrom, during the culturing period, environmental stimulus capable of inducing a desired state of cell, for example, a chemical substance, a low-oxygen stress and/or a temperature stress may be imparted according to necessity to the cell as an assay object. As a result, in accordance with environmental stimulus imparted to the cell, the enhancer/promoter activated in response to the stimulus accelerates the iNOS gene transcription/translation, so that an iNOS protein is synthesized. The iNOS protein synthesizes nitrogen monoxide (NO.) from intracellular L-arginine. The state of the cell may be determined by measuring the amount of nitrogen monoxide synthesized.

For example, when the synthesis of nitrogen monoxide has been determined or when the amount of nitrogen monoxide synthesized has been increased, it is seen that the enhancer/promoter introduced in the cell has been activated. Namely, it is judged that the state or environment of the cell is the state or environment in which the enhancer/promoter is activated. Therefore, for example, if the state or environment in which the enhancer/promoter is activated is the cancerization of the cell, it is predicted that the cell has been cancerized, or that the possibility of the cancerization of the cell is high. Further, for example, if the state or environment in which the enhancer/promoter is activated is a low-oxygen environment, it is judged that the cell lies in a low-oxygen environment, depending on the production of a free radical or the magnitude of free radical production.

Nitrogen monoxide can be measured by a method using an electron spin resonance apparatus or a method using a fluorescent probe specific to nitrogen monoxide. In the method using an electron spin resonance apparatus, nitrogen monoxide may be directly measured, or alternatively the measuring may be performed after trapping nitrogen monoxide by means of a specific spin trapping agent. As the spin trapping agent for nitrogen monoxide, there can be mentioned, for example, N-methylglucamine dithiocarbamate (MGD), diethyl dithiocarbamate (DETC), N-dithiocarboxylsarcosine (DTCS) or carboxy-PTIO. The nitrogen monoxide produced in a cell can be quantitatively measured by exposing any of these spin trapping agents to the cell and thereafter performing measurement using an electron spin resonance apparatus. As the fluorescent probe specific to nitrogen monoxide, there can be mentioned, for example, diaminofluorescein (DAF2) or its derivative. The nitrogen monoxide produced in a cell can be quantitatively measured by exposing such a fluorescent probe to the cell and thereafter performing measurement using a fluorometric instrument.

[System for Detecting the Activity of the Transcriptional Regulatory Sequence in a Tissue by Means of Produced Free Radical]

A cell in which the transcriptional regulatory sequence of a particular gene has been activated can be detected within a tissue by using the vector of this embodiment. As a mode of this embodiment, a method in which the state of a cell is assayed by using a vector having an iNOS gene incorporated therein and producing nitrogen monoxide as a free radical will be described below. First, a vector obtained by incorporating a target promoter in pSV40-NOS2 vector upstream of SV40 promoter, a spin trapping agent and a cationic lipid are mixed together to thereby enclose the vector and the spin trapping agent in lipid membrane vesicles. As the spin trapping agent for nitrogen monoxide, there can be mentioned, for example, N-methylglucamine dithiocarbamate, diethyl dithiocarbamate, N-dithiocarboxylsarcosine or carboxy-PTIO. The lipid membrane vesicles enclosing the vector and the spin trapping agent are probabilistically brought into a tissue and fused with the cell membrane by direct application to the tissue or diffusion into the blood, thereby transporting the contents into the cells. These operations may be performed outside an electron spin resonance (ESR) apparatus. However, it is preferred to make preparations for conducting the detection by means of ESR apparatus after the operation of introducing the vector and the spin trapping agent into the living organism.

Subsequently, by allowing them to stand still for an arbitrary period of time, the activation of the transcription of the vector is realized in cells in which the target promoter is activated, thereby inducing the expression of an iNOS protein. As the iNOS protein synthesizes nitrogen monoxide from intracellular L-arginine, nitrogen monoxide is produced in accordance with the degree of the activation of the target promoter. Produced nitrogen monoxide is trapped by the spin trapping agent having been introduced together with the vector in the cells. After an arbitrary period of time, microwaves of an arbitrary frequency are oscillated from a signal source, and a spin signal specific to the spin trapping agent is detected. Simultaneously, by acquiring the locational information on a signal acquisition site, the spin signal detection site can be identified. These operations are illustrated in FIG. 8.

Referring to FIG. 8, the operations will be described. First, the reporter gene construct and a radical spin trapping agent are provided for a subject tissue. These are mixed with a cationic lipid, thereby being enclosed in lipid membrane vesicles. Subsequently, the contents of the obtained lipid membrane vesicles are brought into contact with an in vivo tissue, thereby accomplishing probabilistic introduction into cells. Incubation is performed for a duration required to realize the expression of the reporter gene of the introduced reporter gene construct and the production of a free radical. Microwaves are oscillated to the subject tissue, and a radical-specific spectrum is detected with respect to the spin trapping agent. Information on the location of spectrum detection in the tissue is detected. The site of radical production in the tissue is identified on the basis of information on detected spectra and the detection location information. As a result, the cells in the environment in which the transcriptional regulatory sequence is activated in the tissue can be detected.

In this embodiment, the detection of a free radical, namely, the detection of a radical-specific spectrum is performed parallel to the acquisition of locational information within the tissue as a cell assembly, or performed before or after the acquisition. The identification of relevant cells is performed by correlating the detection of a free radical with the locational information.

The free radical from the reporter gene can be measured by using, for example, an electron spin resonance (ESR) measuring apparatus. The measurement using the electron spin resonance measuring apparatus can realize not only the in vitro detection of a cell group, tissue and/or tissue segment containing cells to be detected but also the in vivo detection of a cell and/or tissue contained in a living organism.

[Electron Spin Resonance Measuring Apparatus]

The magnetic resonance measuring apparatus according to an embodiment is an apparatus for testing or measuring an object to be measured by using a magnetic resonance, such as nuclear magnetic resonance (NMR) and/or electron spin resonance (ESR), with respect to a detection target.

Figure 4:
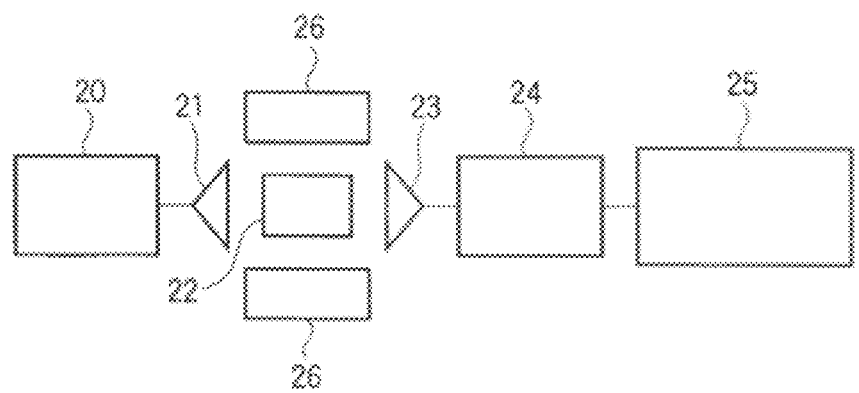
FIG. 4 is a block diagram showing a form of magnetic resonance measuring apparatus according to still a further embodiment.

Referring to FIG. 4, the principle of the magnetic resonance measuring apparatus according to an embodiment will be explained. The magnetic resonance measuring apparatus comprises a signal source (20) configured to output microwave signals. A transmitter (21) is connected to the signal source (20) and is configured to transmit the signals from the signal source to a testing sample as an object to be measured. A receiver (23) is disposed opposite to the transmitter (21) so as to locate the testing sample (22) between the same and the transmitter (21). The receiver (23) is configured to receive the signals from the testing sample (22). A narrow-band filter (24) with bandwidth (BW) MHz is connected to the receiver (23), and configured to amplify the signals having reached the same via the bandpass filter from the receiver (23) and process the amplified signals on the basis of preset information. A magnetic field generator (26) is configured to apply a magnetic field to the testing sample (22).

The signal source (20) may include a signal source capable of outputting microwave signals, an amplifier capable of amplifying the signals from the signal source and a transmitter capable of transmitting the amplified signals to the testing sample. The transmitter (11) may be any of transmitters directional to the testing sample, which are in themselves known. For example, it may be a transmitting antenna.

The magnetic field generator (26) may be any of magnetic field generators capable of applying a magnetic field to the testing sample. As the magnetic field generator (26), use can be made of, for example, any of magnetic field generators generally used in NMR and EST apparatuses.

The receiver (23) may be any of receivers capable of receiving the signals forwarded via the testing sample, which are in themselves known. For example, it may be a receiving antenna.

The narrow-band filter (24) provides means for separating signals of desired frequency from the signals sent from the receiver (23).

Figure 5:
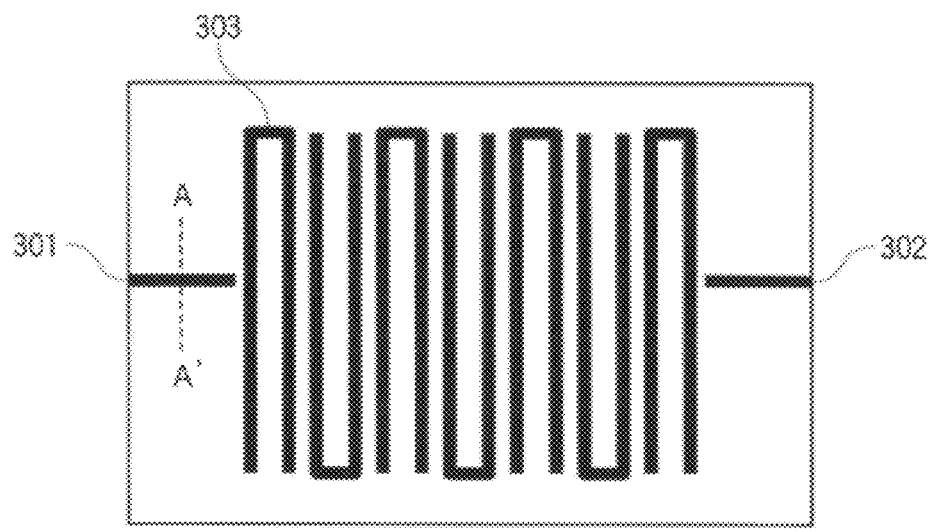
FIG. 5 is a view showing a form of layout of superconducting filter according to still a further embodiment.
Figure 6:
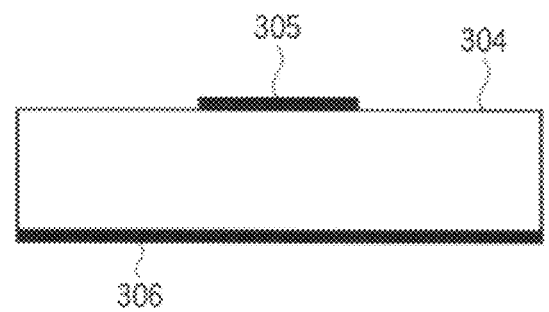
FIG. 6 is a view showing a form of layout of superconducting filter according to still a further embodiment.

With respect to the narrow-band filter, an example of the layout thereof is shown in FIG. 5, and the A-A' sectional structure thereof is shown in FIG. 6. The narrow-band filter comprises, for example, a 7-combline resonator (303) using a microstrip line. The microstrip line is a common waveguide for high frequency including input line (301) and output path (302) pieces as signal bodies provided on a first surface of a dielectric substrate (304) so as to locate on both sides of the resonance electrode (305) and a ground (306) provided on a second surface of the dielectric substrate (304). The length of the combline resonator (303) determines the resonant frequency, and as a filter, determines the center frequency of pass-band. The bandwidth can be determined by optimizing the distance between the combline resonator (303) and the input line (301) or output path (302) and the distance between the combline resonators (303). In this filter, a superconductor may be used in a signal conductor and ground conductor of superconductive filter.

As the superconductors, use can be made of various materials, such as $Nb_3Sn$, $MgB_2$, yttrium high-temperature superconductors ($YBa_2Cu_3O_{7-x}$) and bismuth high-temperature superconductors ($Bi_2Sr_2CaCu_2O_{8+x}$, $Bi_2Sr_2Ca_2Cu_3O_{10+x}$).

In the conventional early stage of diseases, the number of cells placed in the state of a pre-disease process in which the promoter activity is changed in a target tissue is small. Therefore, the probability of these cells contained in the cells collected for in vitro diagnosis would not be high, so that it is required to in vivo detect the promoter activity. As the currently practiced in vivo imaging technology for promoter activity, there are a method in which luciferase luminescence is detected by using ultrahigh-sensitivity CCD and a method in which the fluorescence of GFP or the like is detected by fluorescent molecular tomography. However, these methods all use optical detection. Therefore, the luminescence and/or fluorescence in a deep area (approximately 2 cm or more) of the body is attenuated, so that the application of the methods is limited only to the detection for small animals in which the activity within a tissue of approximately 2 cm or less thickness is detected.

When as in this embodiment a free radical is used as an indication, the detection can be effected without being limited to optical means. By the application of non-optical means, it is practicable to detect the activation or non-activation of the transcriptional regulatory sequence, such as the promoter and/or enhancer, or measure the degree of the activation in not only the conventional shallow area of a sample, such as a living organism, but also a deep area thereof. This makes it feasible to find a target disease, for example, cancerization in an early stage. Further, by the measurement using the reporter gene construct in combination with the electron spin resonance measuring apparatus according to this embodiment, it is practicable to non-invasively detect the activation or non-activation of the transcriptional regulatory sequence, such as the promoter and/or enhancer, in a deep area of a sample. The detection method using the reporter gene construct in combination with the electron spin resonance measuring apparatus according to this embodiment can realize an earlier diagnosis of disease with higher accuracy.

Moreover, for example, in the detection of early cancerized cells, it is practicable to injure disease cells by the use of a free radical produced from the reporter gene construct, simultaneously with the detection of the cells. This cytotoxicity can be altered by arbitrarily selecting the time of trapping of the reporter gene construct in the cells, the type of the reporter gene contained therein, the type of the radical emitted and the amount thereof.

Further, similarly, a particular cell, for example, a cell with a particular environment or state can be detected in a cell assembly, such as a cell group, a tissue or a living organism. By using the radical as a reporter, the particular cell can be detected in a manner non-invasive to the object to be measured. This detection method can realize advantageous detection of a particular cell in various conditions, for example, in vivo, in vitro and ex vivo conditions.

In this embodiment, the detection of a free radical in a cell assembly is performed in parallel to the acquisition of free radical detection locational information in the cell assembly. However, the acquisition of free radical detection locational information may be performed in advance of the detection of produced free radical or subsequent to the detection thereof. The detection of a particular cell in the cell assembly may be performed by, for example, identifying the site of free radical production through correlating of the information on free radical production with the free radical detection locational information in the cell assembly. The detection of a free radical may be judged by the production or non-production of a free radical or by a change in the amount of produced free radical.

[Assay Kit]

An assay kit for use in the method of assaying the activation or non-activation of the transcriptional regulatory sequence or the degree of the activation thereof by the use of the reporter gene construct and the electron spin resonance measuring apparatus according to this embodiment is also provided.

The assay kit may be any one comprising any of the above reporter gene constructs and a spin trapping agent responsive to the reporter gene contained therein. For example, when the reporter gene is any of NOSs, the spin trapping agent may be any agent for trapping nitrogen monoxide, for example, at least one spin trapping agent selected from the group consisting of N-methylglucamine dithiocarbamate, diethyl dithiocarbamate, N-dithiocarboxylsarcosine or carboxy-PTIO. With respect to the electron spin resonance measuring apparatus, the simultaneous measurement of different radical species can be performed by constructing the apparatus in which a plurality of narrow-band filters and receiving circuits are included. This assay kit may comprise reporter gene constructs respectively containing multiple types of reporter genes and spin trapping agents responsive to the radical species produced by the individual reporter genes thereof. This assay kit may further comprise a lipid for enclosing the reporter gene construct and the spin trapping agent to thereby form lipid membrane vesicles. This lipid may be, for example, an ion complex carrier, such as a cationic lipid, a basic polymer, a synthetic polypeptide or apatite carbonate. This assay kit may still further comprise an instruction manual and/or a container for forming lipid membrane vesicles.

This assay kit is advantageous in conveniently and/or rapidly practicing any intended method.

EXAMPLE

Example 1

Construction of iNOS Vector

An iNOS vector in which nitrogen monoxide synthase 2 (iNOS) gene was used as a reporter gene was constructed. PGV-P2 vector (Toyo B-Net Co., Ltd.) carrying an expression cassette comprising simian virus 40 (SV40) early promoter, firefly luciferase gene and SV40 poly(A) addition signal was digested with restriction enzyme Hin dIII, and the 5' protruding end was blunt-ended with the Klenow fragment of $E.$ $coli$ DNA polymerase. The resultant vector was digested with restriction enzyme Xba I, thereby obtaining a PGV-P2 vector fragment devoid of the luciferase gene. The iNOS gene of a mouse was incorporated in this vector fragment. Namely, pSPORT6 vector (pNOS2) having the cDNA sequence of mouse iNOS gene incorporated therein was purchased from Life Technologies, and digested with restriction enzymes Sma I and Xba I, thereby obtaining a cDNA fragment of iNOS gene. This cDNA fragment was ligated to the above obtained PGV-P2 vector fragment with the use of T4 ligase, thereby obtaining an iNOS vector: pSV40-NOS2 (FIG. 1).

Example 2

Detection of Nitrogen Monoxide (NO.) Having Responded to Carcinogenicity by iNOS Vector An enhancer region responsive to a carcinogenic substance was incorporated in the iNOS vector: pSV40-NOS2. The enhancer region of cytochrome 1A1 gene responsive to a carcinogenic substance (benzopyrene) (SEQ ID NO: 4) was amplified by PCR from a mouse genome. The 5' terminal of the amplified enhancer region was phosphorylated with T4 polynucleotide kinase, and ligated using T4 ligase to pSV40-NOS2 having been digested with restriction enzyme Sma I and having its 5' terminal dephosphorylated with alkali phosphatase, thereby obtaining pXRE-SV40-NOS2 (FIG. 2). Using this vector, the correlation of the activation of the enhancer region by a carcinogenic substance with the amount of nitrogen monoxide (NO.) synthesized by iNOS was studied.

Figures 3A, 3B:
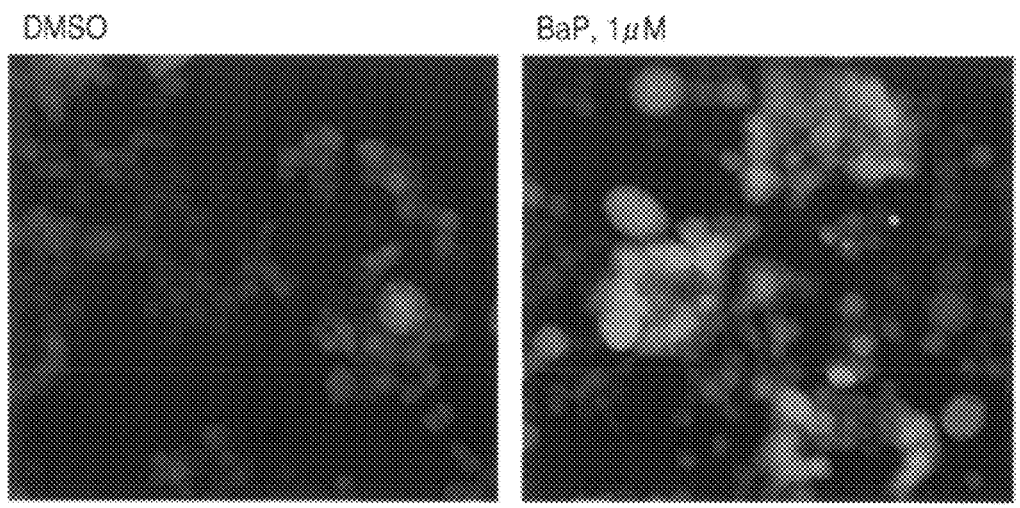
FIG. 3A is a view showing the results of Example 2 according to a further embodiment.
FIG. 3B is a view showing the results of Example 2 according to a further embodiment.

Mouse neuroblastoma Neuro2a (American Type Cell Culture) was seeded on a 24-well plate at a density of $8.0 \times 10^4$ cells/well, and using DMEM/F12 medium (DF1:1 medium) supplemented with 10% fetal calf serum (FCS), cultured overnight in a 5% $CO_2$ atmosphere at 37° C. Separately, lipofectamine 2000 (Life Technologies) was added in an amount of 2.0 µL to 50 µL of Opti-MEM medium, and incubated at room temperature for 5 minutes. The resultant solution was mixed with 50 µL of Opti-MEM medium loaded with 0.8 µg of pXRE-SV40-NOS2, and incubated at room temperature for 20 minutes. The mixture was added to the overnight cultured Neuro2a, and cultured in a 5% $CO_2$ atmosphere at 37° C. Twenty four (24) hours later, the medium of Neuro2a was removed, and DF1:1 medium (10% FCS) containing 1.0 µM of dimethyl sulfoxide (DMSO) or benzopyrene (BaP) was added, and the mixture was cultured in a 5% $CO_2$ atmosphere at 37° C. Twenty four (24) hours later, the medium was removed, and the culture was washed with DF1:1 medium (without FCS) twice. Thereafter, DF1:1 medium (without FCS) containing 10 µM of diaminofluorescein-2-diacetate (DAF2-DA, Sekisui Medical) being a fluorescent probe for the detection of nitrogen monoxide (NO.) was added and incubated at 37° C. Two hours later, the cells were washed with phosphate buffer (PBS) twice, and the fluorescence by the reaction product of DAF-2DA and nitrogen monoxide (NO.) (DAF-2T, excitation wavelength: 495 nm, fluorescence wavelength: 515 nm) was observed by means of an inverted fluorescence microscope. FIG. 3A shows the results obtained when dimethyl sulfoxide (DMSO) was added. FIG. 3B shows the results obtained when benzopyrene (BaP) was added.

As seen from FIGS. 3A and 3B, the induction of fluorescence by an increase of the amount of nitrogen monoxide (NO.) synthesized was observed in the cells exposed to benzopyrene. Thus, the correlation between the activation of enhancer region by benzopyrene and the increase of the amount of produced nitrogen monoxide (NO.) by iNOS was exhibited.

Example 3

Construction of Mutant-Type iNOS Vector

First, pNOS2 was cleaved with restriction enzymes Sal I and Eco RV, thereby obtaining a fragment of iNOS gene containing the 5'-untranslated region and the coding region. This fragment was incorporated in pBluescriptII SK(−) vector having been cleaved with restriction enzymes Sal I and Eco RV, thereby obtaining pNOS2-RV. Subsequently, a DNA fragment having the 3'-terminal side of iNOS gene altered was amplified by PCR employing a mutant primer with the use of pNOS2 as a template. Mutation was introduced in reverse primers, and the same forward primer was used. The DNA sequences of the forward primer and reverse primers in which two types of mutations were introduced are shown below.

```
Forward primer:
                                  (SEQ ID NO: 5)
5'-GGCAGAGATTGGAGGCCTTGTGT Reverse primer 1:
                        (SEQ ID NO: 6, iNOStr)
5'-AGGTCTAGATTCAACCGAAGATATCTTCAT Reverse primer 2:
                         (SEQ ID NO: 7, iNOS-F)
5'-CTCTGTCTAGACCGAGCCTCGTGGCTTTGGGC
```

With respect to the iNOStr, for the deletion of 21 amino acid residues from the carboxy terminal (C-terminal) of wild-type iNOS, the mutation for substituting the stop codon (nucleotides 3476 to 3478) of wild-type iNOS with glycine was introduced in the reverse primer. With respect to the iNOS-F, for the addition of V5-polyhistidine-tag sequence to wild-type iNOS, the mutation for removing the stop codon of wild-type iNOS was introduced in the reverse primer. A restriction enzyme recognition sequence (Stu I or Xba I recognition sequence) was added to the primers in order to facilitate the cloning of amplified fragment.

DNA fragments having been amplified by PCR using these primers were cleaved with Stu I and Xba I, and incorporated in the pNOS2-RV having been cleaved with Stu I and Xba I, thereby obtaining two mutant-type iNOS genes (piNOStr and piNOS-F).

Figure 9A:
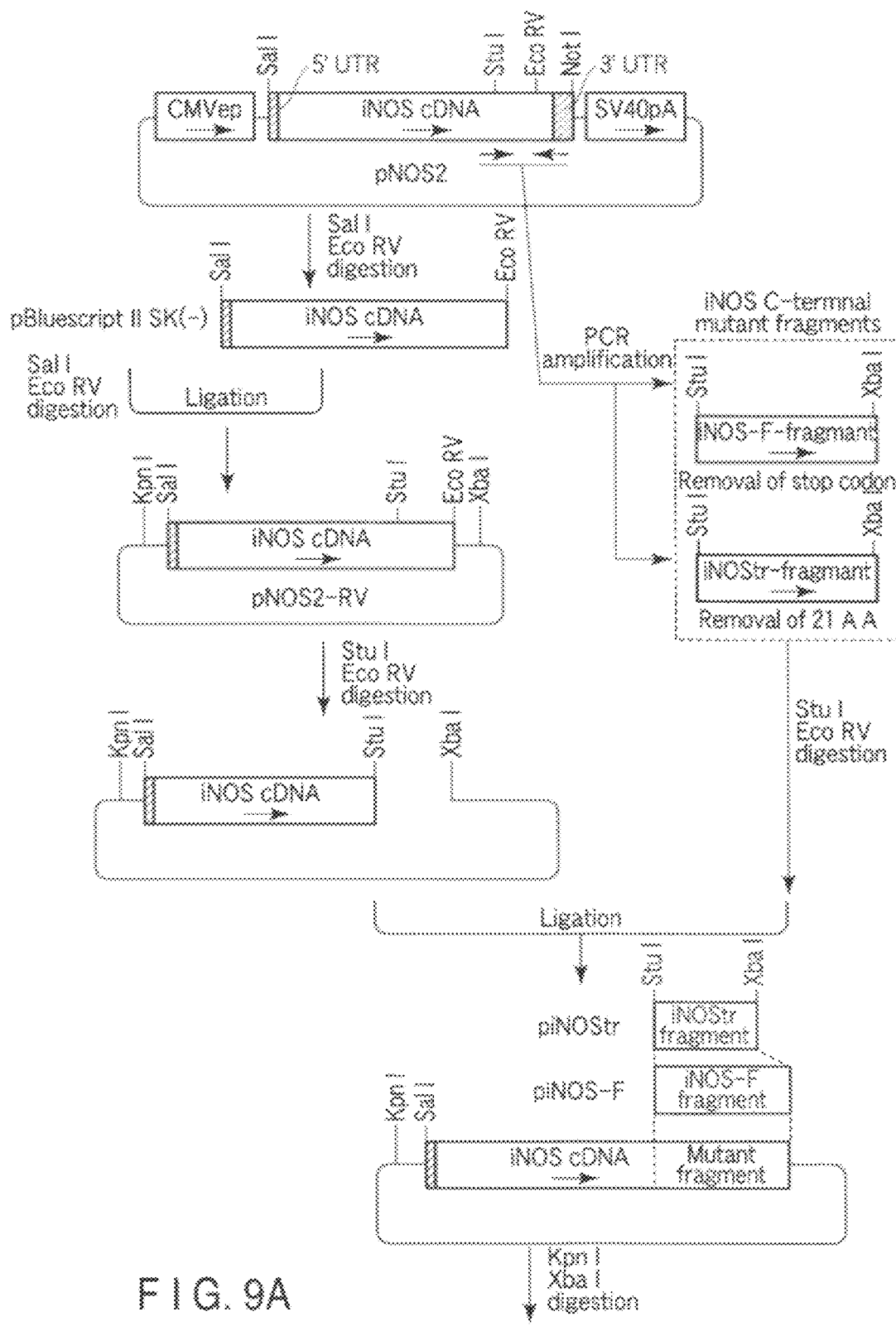
FIG. 9A is a view showing pCMV-iNOStr and pCMV-iNOS-F as forms of vector.
Figure 9B:
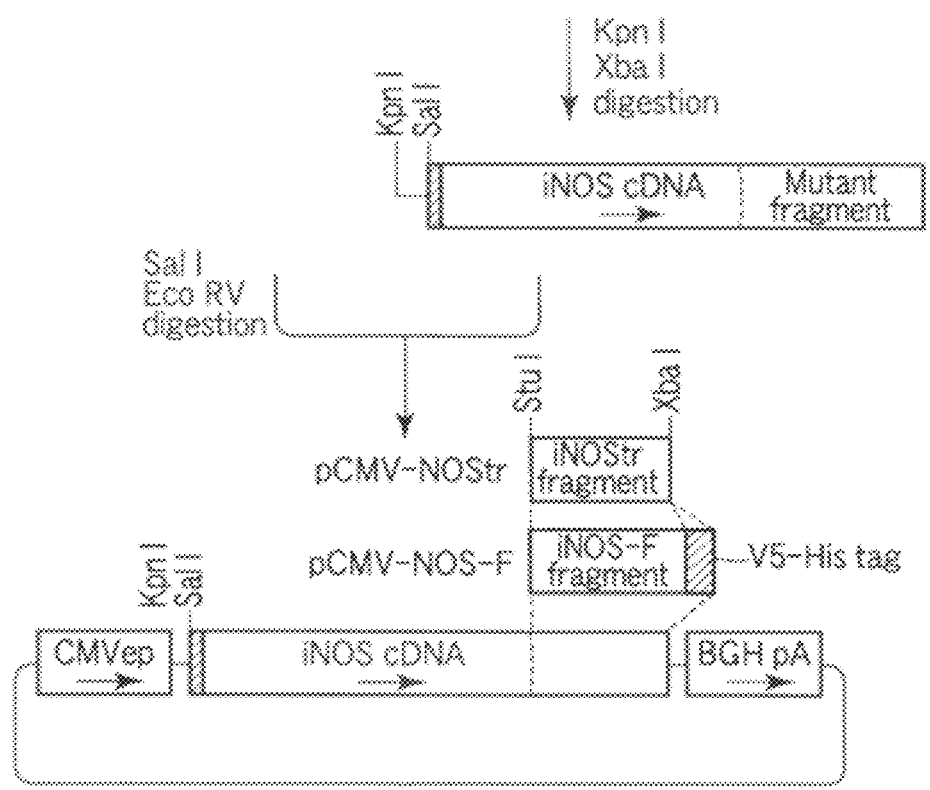
FIG. 9B is a view showing pCMV-iNOStr and pCMV-iNOS-F as forms of vector.

Finally, piNOStr and piNOS-F were cleaved with Kpn I and Xba I to thereby take out mutant iNOS genes, and incorporated in the pcDNA4/V5-His B (Life Technologies) having been cleaved with Kpn I and Xba I, thereby obtaining mutant-type iNOS vectors: pCMV-iNOStr and pCMV-iNOS-F. The outline of these operations are shown in FIG. 9A and FIG. 9B. FIG. 9B is continuous from FIG. 9A (FIG. 9A and FIG. 9B). The arrow appearing in the lowermost zone of FIG. 9A and the description appearing on the right side thereof indicate the same "digestion" treatment as the arrow appearing in the uppermost zone of FIG. 9B and the description appearing on the right side thereof. This is intended to facilitate the understanding of the continuity of the description contents from FIG. 9A to FIG. 9B.

Example 4

Detection of Nitrogen Monoxide (NO.) by Mutant-Type iNOS Vector

Figure 10A:
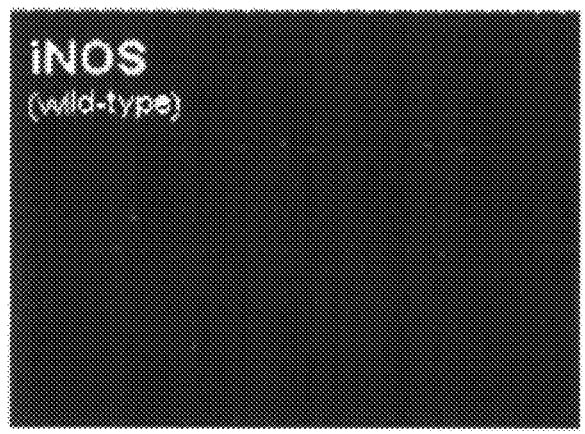
FIG. 10A is a view showing the results of Example 4.
Figure 10B:
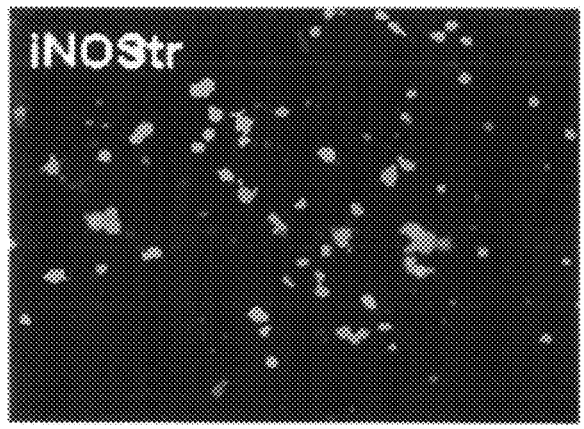
FIG. 10B is a view showing the results of Example 4.
Figure 10C:
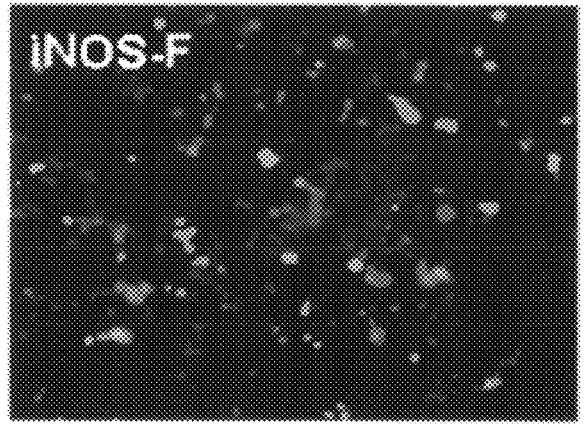
FIG. 10C is a view showing the results of Example 4.

Mouse neuroblastoma Neuro2a (American Type Cell Culture) was seeded on a 24-well plate at a density of $8.0 \times 10^4$ cells/well, and using DMEM/F12 medium (DF1:1 medium) supplemented with 10% fetal calf serum (FCS), cultured overnight in a 5% $CO_2$ atmosphere at 37° C. Separately, lipofectamine 2000 (Life Technologies) was added in an amount of 2.0 µL to 50 µL of Opti-MEM medium, and incubated at room temperature for 5 minutes. The resultant solution was mixed with 50 µL of Opti-MEM medium loaded with 0.8 µg of wild-type or mutant-type iNOS vector (pCMV-iNOStr, pCMV-iNOS-F, pNOS2), and incubated at room temperature for 20 minutes. The mixture was added to the overnight cultured Neuro2a, and cultured in a 5% $CO_2$ atmosphere at 37° C. Twenty four (24) hours later, the medium of Neuro2a was removed, and the culture was washed with DF1:1 medium (without FCS) twice. Thereafter, DF1:1 medium (without FCS) containing 10 µM of diaminofluorescein-2-diacetate (DAF2-DA, Sekisui Medical) being a fluorescent probe for the detection of nitrogen monoxide (NO.) was added and incubated at 37° C. Two hours later, the cells were washed with phosphate buffer (PBS) twice, and the fluorescence by the reaction product of DAF-2DA and nitrogen monoxide (NO.) (DAF-2T, excitation wavelength: 495 nm, fluorescence wavelength: 515 nm) was observed by means of an inverted fluorescence microscope. FIG. 10A shows the results with respect to the cells in which the wild-type iNOS was introduced. FIG. 10B and FIG. 10C show the results with respect to the cells in which the mutant-type iNOSs were introduced. Specifically, FIG. 10B shows the results with respect to the cells in which pCMV-iNOStr was introduced, and FIG. 10C shows the results with respect to the cells in which pCMV-iNOS-F was introduced.

As seen from FIG. 10A, FIG. 10B and FIG. 10C, the increase of fluorescence by an increase of the amount of nitrogen monoxide (NO.) synthesized was observed in the cells in which the mutant-type iNOSs were introduced (cells in which pCMV-iNOStr was introduced and cells in which pCMV-iNOS-F was introduced). Thus, it was exhibited that the mutant-type iNOSs had a capability of producing nitrogen monoxide (NO.) higher than that of the wild-type iNOS.

Example 5

Assay Kit

An assay kit is provided by combining assay kit components comprising a reporter gene construct containing a NOS gene as the reporter gene, N-methylglucamine dithiocarbamate (MGD), a cationic lipid, a container for forming lipid membrane vesicles and an instruction manual and packing the components in a resin packing material.

Example 6

Example of Electron Spin Resonance Measuring Apparatus

Figure 7:
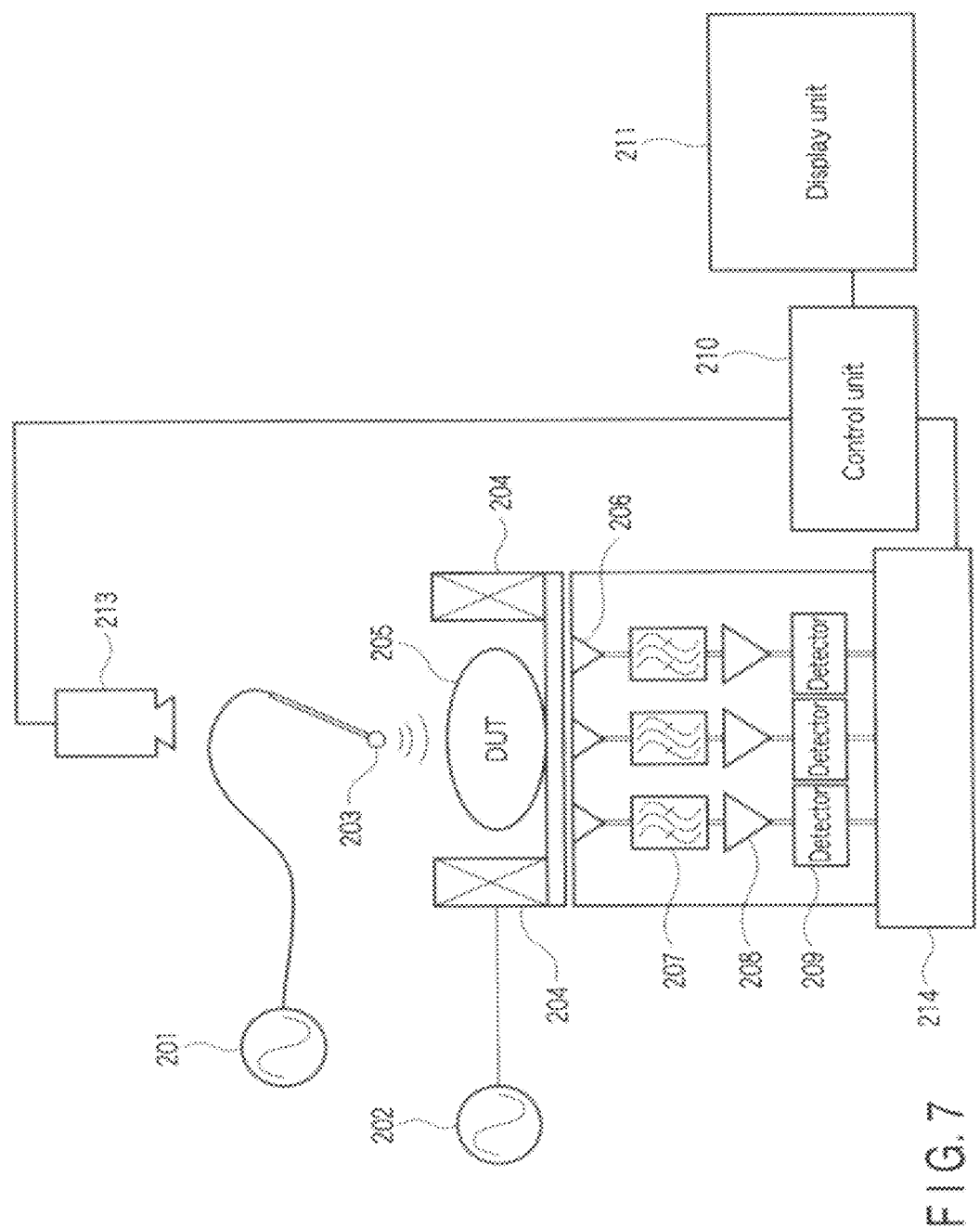
FIG. 7 is a block diagram showing an example of electron spin resonance measuring apparatus according to still a further embodiment.

FIG. 7 is a schematic block diagram showing an example of electron spin resonance measuring apparatus for use in the detection of cells using the reporter gene construct.

The electron spin resonance measuring apparatus of FIG. 7 comprises, as a signal source, a transmission signal generator (201) including a transmission circuit configured to produce microwaves and an amplifier capable of amplifying the produced microwaves. The signal from the transmission signal generator (201) is forwarded via an operating transmitting antenna (203) to an object to measured (205) and applied thereto. In advance of the application, lipid membrane vesicles are provided by mixing the reporter gene construct and the radical spin trapping agent with the cationic lipid to thereby attain the enclosure in membrane vesicles. The lipid membrane vesicles are added to a measurement area of the measurement object (205), so that the reporter gene construct enclosed in the lipid membrane vesicles is introduced in the cells of the area. Incubation is performed for a period of time required for the expression of the reporter gene of the introduced reporter gene construct and the production of a free radical. Thereafter, the signal application to the measurement object (205) is performed.

In that instance, the measurement object (205) is located in the magnetic field generated by a magnetic field generator (204). The magnetic field generator (204) is controlled by a magnetic field modulator (202), so that the magnetic field can be modulated. The signal from the signal-applied measurement object (205) within the magnetic field is received by a receiving antenna (206). In that instance, the locational information on the transmitting antenna (203) is obtained from an image input unit (213) as a locational information detector being means for detecting the location of the transmitting antenna. The locational information is forwarded to a controller (210). By the control by the controller (210) on the basis of obtained locational information, a movable receiver (230) is moved. Namely, by the control by the controller (210), a receiver moving unit (212) supporting the receiver (230) is moved, and accordingly the location of the receiver (230) is moved. The receiver (230) receives the signal from the measurement object (205) to which the signal from transmitting antenna (203) has been applied within the magnetic field. The receiver (230) comprises a receiving antenna (206), a narrow-band filter (207) connected thereto, a low-noise amplifier (208) connected to the narrow-band filter and a detector (209) connected to the low-noise amplifier. The signal received by the receiving antenna (206) is branched by the narrow-band filter (207). The resultant branched signal is amplified by the low-noise amplifier (208), and forwarded to the detector (209). The detector (209) includes a frequency converter by a mixer, a local signal source, etc. and a signal processing circuit. In the detector (209), the frequency of the forwarded signal is converted by the frequency converter. The signal whose frequency has been converted is processed by the signal processing circuit on the basis of the magnitude of the signal, the locational information and information on images, etc. obtained from the image input unit (213) and the information of in-advance stored program and/or table, etc. The processed information is displayed on a display unit (211).

The electron spin resonance measuring apparatus according to this embodiment allows to effect evaluation while changing the measurement cross-section location of the measurement object (205) from the transmitting antenna (203) and the receiving location of the receiving antenna (206). In that instance, in each measurement cross-section location, it is also practicable to effect evaluation while modulating the magnetic field by controlling the magnetic field generator (204) by means of the magnetic field modulator (202). The control of the magnetic field modulator (202) may be performed by the controller (210) on the basis of the information of in-advance stored program and/or table, etc., or may be performed on the basis of the information having been inputted by an operator from an input unit (not shown in the drawing) connected to the controller. The controller may be a computer.

The detector (209) includes a frequency converter by a mixer, a local signal source, etc. and a signal processing circuit, for example, a computer or the like. This signal processing circuit may be disposed in a form unified with other constituent elements of the magnetic resonance measuring apparatus, such as the detector (209) and/or the controller (210). Alternatively, the signal processing circuit may be disposed in a form connected in a fashion allowing mutual signal transmission and receiving as a constituent element separate from the other constituent elements. The signal processing circuit may be, for example, a computer.

The display of information on a display unit (211) may be effected in a fashion such that the image from the image input unit (213) is combined with the evaluation information based on measured magnetic resonance signal.

The transmitting antenna may be grasped by an operator and moved to any arbitrary location. Alternatively, the transmitting antenna may be fixed on a movable support and may be moved to any arbitrary location by the hand power of an operator or by the control by the controller.

When it is intended to prepare two-dimensional sliced images or three-dimensional imaging graphics, the same means as in common MRI and like equipments can be utilized. For example, it is practicable to apply, apart from a magnetostatic field, a magnetic field having a strength proportional to a distance (namely, gradient magnetic field) and obtain information on changes of electron spin phase and frequency by the gradient magnetic field. As a product of synthesis of individual signals is actually observed, in analyzing of obtained signal, it is appropriate to disintegrate the same into individual locational signals (namely, proportional to the electron spin in each location) by conducting two-dimensional or three-dimensional Fourier transform, thereby obtaining image information. Display can be realized in such a manner that on the basis of the obtained image information, the surface information of a measurement object among ESR evaluation informations is fitted on the actual image of an image input unit or is superimposed on separately acquired information of MRI, X-ray CT or the like. This makes it feasible to present an increased amount of information. When it is intended to impart such functions to the magnetic resonance measuring apparatus, according to necessity, constituent elements which are in themselves publicly known are added to the constituent elements of the magnetic resonance measuring apparatus.

In the above-mentioned example, the location of the transmitting antenna is identified on the basis of image information. However, this is not limitative, and use can be made of any other method of detecting the location of the transmitting antenna which is in itself known, such as a method in which a gyro is housed in the transmitting antenna itself to thereby acquire the data of any displacement from a reference location.

Conventionally, the electron spin resonance method can be used to detect a weak electron spin signal within the body as a non-optical detection means. However, to date, there is no report with respect to the method of detecting a particular promoter activity by the electron spin resonance method.

By combining the electron spin resonance measuring apparatus according to this embodiment with the above-described reporter gene construct, target diseases, for example, cancerization can be discovered at an early date, and the disease occurring in a deep area of a living organism can be detected non-invasively. For example, any change of gene transcription environment occurring in the event of the conversion of normal stem cells to cancerous stem cells by chronic inflammation can be detected in living organisms. Therefore, earlier diagnosis of diseases with greater accuracy can be realized by the detection method in which the electron spin resonance measuring apparatus is combined with the reporter gene construct according to the foregoing embodiments.

According to the foregoing embodiments, a particular promoter within a tissue can be detected and can be utilized in usages, such as the early diagnosis of diseases. Moreover, there are provided a method in which on the basis of radical production corresponding to promoter activity, a particular promoter activity is detected by an electron spin resonance through the replacement of the same by the amount of radical produced, and an apparatus therefor. These method and apparatus are also involved in the scope of this application.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A reporter gene construct comprising;
 a transcriptional regulatory sequence that is activated dependently of environment; and
 a reporter gene that is operably linked downstream of the transcriptional regulatory sequence, and the reporter gene being a mutant-type iNOS gene comprising SEQ ID NO: 3,
 wherein the reporter gene construct is expressible in a cell, and wherein the reporter gene construct is more active than the wild type iNOS gene.

2. The reporter gene construct according to claim 1, wherein the transcriptional regulatory sequence is an enhancer and/or promoter of a disease-associated gene.

3. The reporter gene construct according to claim 2, wherein the transcriptional regulatory sequence is selected from the group consisting of a myc gene, a fos gene and a ras gene.

4. The reporter gene construct according to claim 1, wherein the transcriptional regulatory sequence is a promoter sequence selected from the group consisting of a cytomegalovirus immediate promoter, a simian virus 40 early promoter and a herpes simplex virus thymidine kinase promoter, and wherein an insertion site of an enhancer of a gene that is activated dependently of environment is further provided upstream of the promoter sequence.

5. The reporter gene construct according to claim 4, wherein the enhancer is an enhancer of a disease-associated gene.

6. The reporter gene construct according to claim 5, wherein the enhancer is an enhancer of a gene selected from the group consisting of a myc gene, a fos gene and a ras gene.

7. The reporter gene construct according to claim 1, wherein a transcription terminator gene is further contained downstream of the reporter gene.

8. A method of predicting an environment of a cell, comprising:
 (1) introducing the reporter gene construct of claim 1 in a cell,
 (2) detecting any free radical produced by the cell obtained in (1), and
 (3) judging the environment of the cell on the basis of results obtained in (2) and then predicting the environment of the cell.

9. The method according to claim 8, wherein the detecting in (2) is carried out by detecting an electron spin resonance spectrum in the presence of a spin trapping agent.

10. A method of detecting a particular cell in a cell assembly, comprising:
 (1) introducing the reporter gene construct of claim 1 in a cell assembly,
 (2) detecting free radical produced in the cell assembly obtained in (1),
 (2a) simultaneously acquiring free radical detection locational information in the cell assembly,
 (3) judging a cell having produced a free radical on the basis of results obtained in (2) and (2a).

11. The method according to claim 10,
 wherein the judging in (3) is carried out by identifying a site of free radical production through correlating of the information on free radical obtained in (2) with the free radical detection locational information acquired in (2a).

12. The method according to claim 10, wherein the detecting in (2) is performed by detecting an electron spin resonance spectrum in the presence of a spin trapping agent.

13. An assay kit comprising;
 (a) a reporter gene comprising;
 a transcriptional regulatory sequence that is activated dependently of environment; and
 a reporter gene that is operably linked downstream of the transcriptional regulatory sequence, and the reporter gene being a mutant-type iNOS gene comprising SEQ ID NO: 3,
 wherein the reporter gene construct is expressible in a cell, and wherein the reporter gene construct is more active than the wild type iNOS gene, and
 (b) a spin trapping agent.

14. The assay kit according to claim 13, wherein the spin trapping agent is selected from the group consisting of N-methylglucamine dithiocarbamate, diethyl dithiocarbamate, N-dithiocarboxylsarcosine and carboxy-PTIO.

15. The assay kit according to claim 13, wherein the transcriptional regulatory sequence is an enhancer and/or promoter of a disease-associated gene.

16. The assay kit according to claim 14, wherein the transcriptional regulatory sequence is selected from the group consisting of a myc gene, a fos gene and a ras gene.

* * * * *